(12) United States Patent
Pierre

(10) Patent No.: US 11,278,543 B2
(45) Date of Patent: Mar. 22, 2022

(54) INHIBITORS OF THE PP1/GADD34 COMPLEX FOR THE TREATMENT OF A CONDITION REQUIRING AN IMMUNOSUPPRESSIVE ACTIVITY

(71) Applicant: Philippe Pierre, Marseilles (FR)

(72) Inventor: Philippe Pierre, Marseilles (FR)

(73) Assignees: INSERM, Paris (FR); UNIVERSITE D'AIX MARSEILLE, Marseilles (FR); CNRS, Paris (FR)

( * ) Notice: Subject to any disclaimer, the term of this patent is extended or adjusted under 35 U.S.C. 154(b) by 0 days.

(21) Appl. No.: 14/969,798

(22) Filed: Dec. 15, 2015

(65) Prior Publication Data

US 2017/0128433 A1    May 11, 2017

Related U.S. Application Data

(60) Continuation of application No. 14/536,080, filed on Nov. 7, 2014, now abandoned, which is a division of application No. 13/511,151, filed as application No. PCT/EP2010/067975 on Nov. 23, 2010, now abandoned.

(30) Foreign Application Priority Data

Nov. 23, 2009    (EP) ..................................... 09306124

(51) Int. Cl.
| | | |
|---|---|---|
| *A61K 31/47* | (2006.01) | |
| *A61K 31/00* | (2006.01) | |
| *A61K 39/00* | (2006.01) | |
| *A61P 37/06* | (2006.01) | |
| *A61K 31/35* | (2006.01) | |

(52) U.S. Cl.
CPC .............. *A61K 31/47* (2013.01); *A61K 31/00* (2013.01); *A61K 31/35* (2013.01); *A61K 39/001* (2013.01); *A61P 37/06* (2018.01); *Y02A 50/30* (2018.01)

(58) Field of Classification Search
None
See application file for complete search history.

(56) References Cited

U.S. PATENT DOCUMENTS

| | | | | |
|---|---|---|---|---|
| 8,129,340 B2* | 3/2012 | Kroemer | ............ | A61K 38/1709 |
| | | | | 514/7.6 |
| 8,236,490 B2* | 8/2012 | Roca | ...................... | C12N 15/81 |
| | | | | 435/254.1 |
| 8,802,721 B2* | 8/2014 | Sun | ...................... | A61K 31/381 |
| | | | | 514/443 |
| 2011/0060120 A1* | 3/2011 | Obeid | ................ | A61K 38/1709 |
| | | | | 530/300 |

FOREIGN PATENT DOCUMENTS

| | | |
|---|---|---|
| JP | 8-188533 | 7/1996 |
| WO | 2008/028965 | 3/2008 |
| WO | 2008/032153 | 3/2008 |

OTHER PUBLICATIONS

Kaser, A., et al. Cell, 2008;134:743-756.*
Nogalska, A., et al. Exp. Neurol. 2007;240:610-618.*
Carr, D. and Tomanek, L. Curr. Top. Microbiol. Immunol. 2006;303:47-65.*
Kaser, A. and Blumberg, R.S. Sem. Immunol. 2009;21:156-153.*
Boyce et al., SCIENCE, 2005, pp. 935-939, vol. 307.
Dombroski et al., Am. J. Hum. Gen., 2010, pp. 719-729, vol. 86.
Wensheng et al., "Enhanced Integrated Stress Response Promotes Myelinating Oligodendrocyte Survival in Response to Interferon-Gamma", The American Journal of Pathology, Nov. 2008, pp. 1508-1517, vol. 173, No. 5.
Chaput et al., "Molecular Determinants of Immunogenic Cell Death: Surface Exposure of Calreticulin Makes the Difference", Journal of Molecular Medicine, Oct. 200, pp. 1069-1076, vol. 85, No. 10.

* cited by examiner

*Primary Examiner* — G. R. Ewoldt
(74) *Attorney, Agent, or Firm* — WC&F IP

(57) ABSTRACT

The present invention relates to the general field of treatment and prevention of diseases involving an inflammatory condition, namely sepsis or infectious or viral diseases as well as diseases requiring for the treatment of immunosuppressive activity namely autoimmune diseases and graft rejection. In particular, the invention relates to an inhibitor of the activity or the formation of the PP1/GADD34 complex for the treatment of a condition requiring an immunosuppressive activity or an anti-inflammatory activity.

16 Claims, 13 Drawing Sheets

Figure 1A:
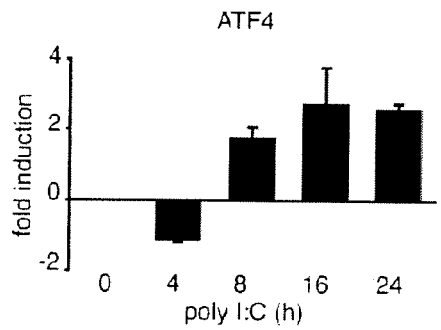
Figure 1A:
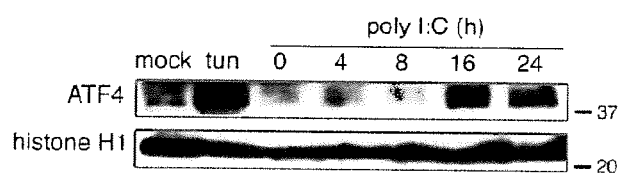
Figure 1B:
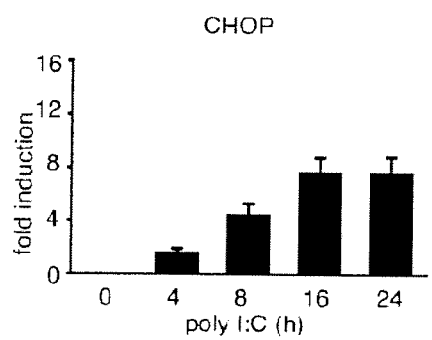

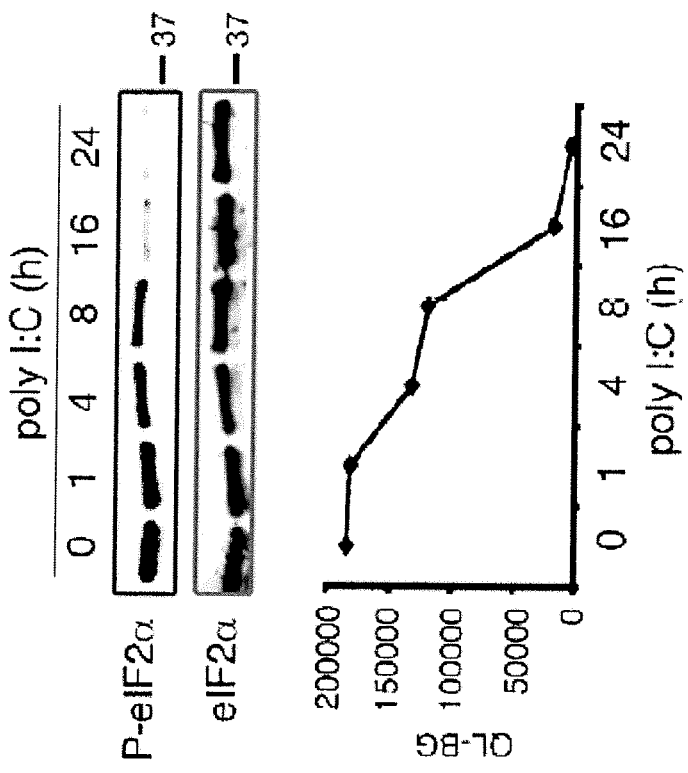
Figure 2B
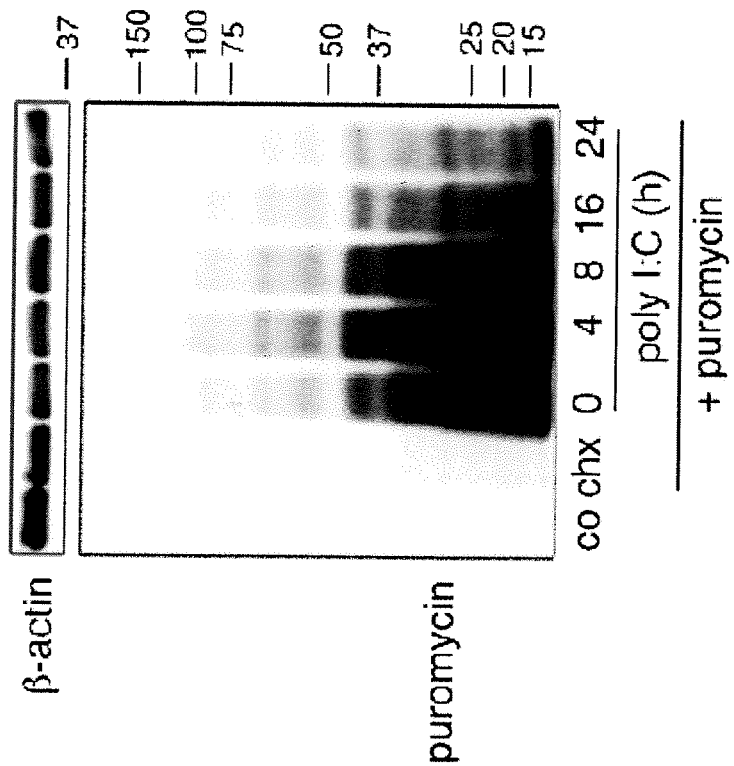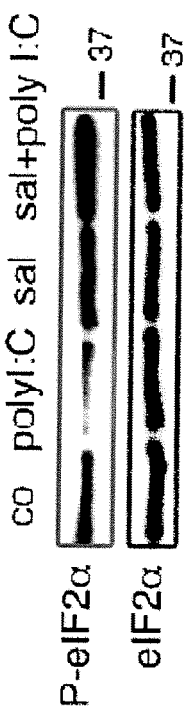
Figure 2A
Figure 2C
Figure 2D

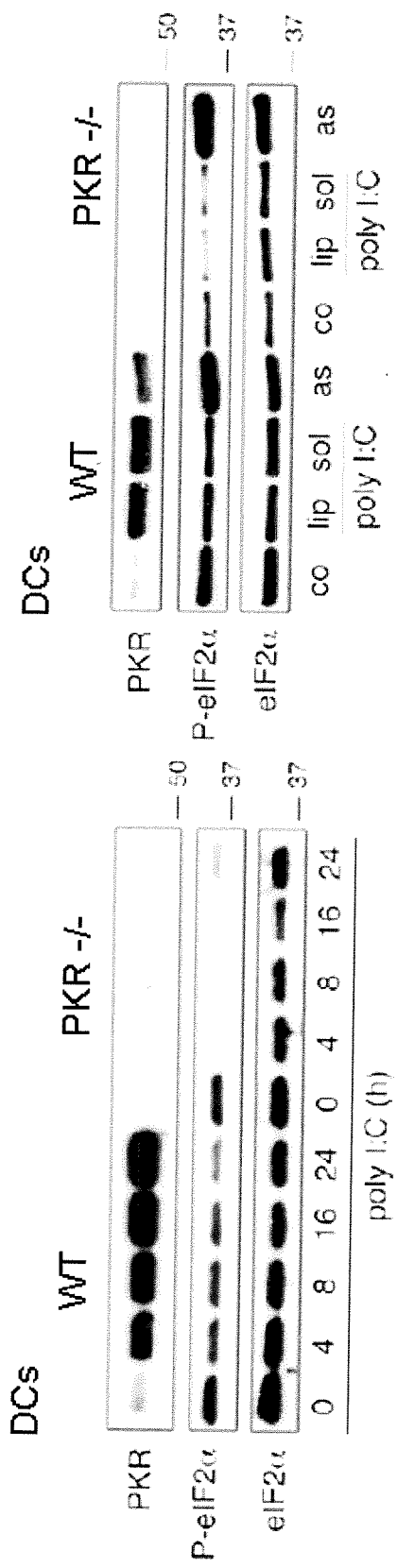
Figure 3A
Figure 3B
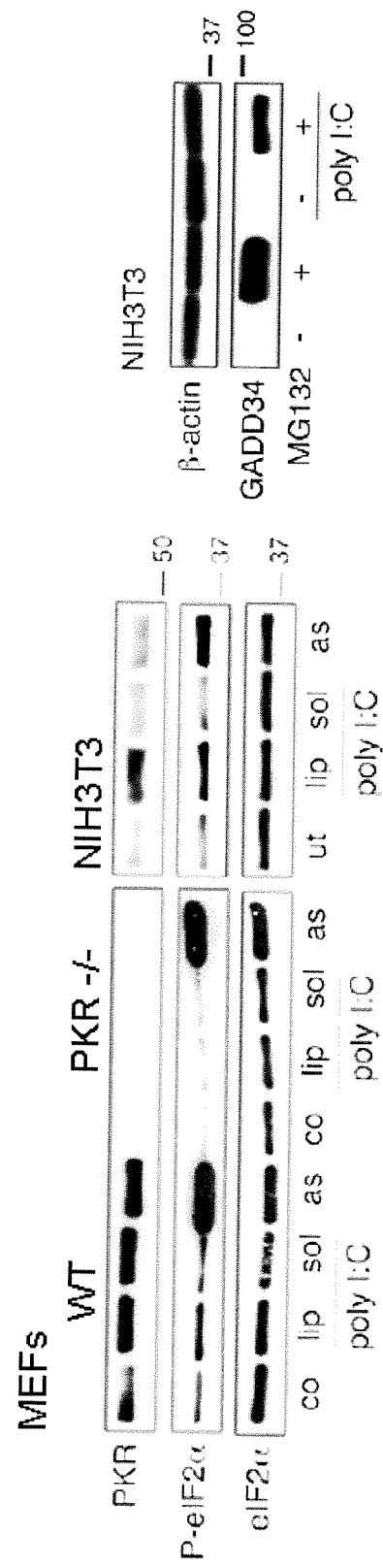
Figure 3C
Figure 3D

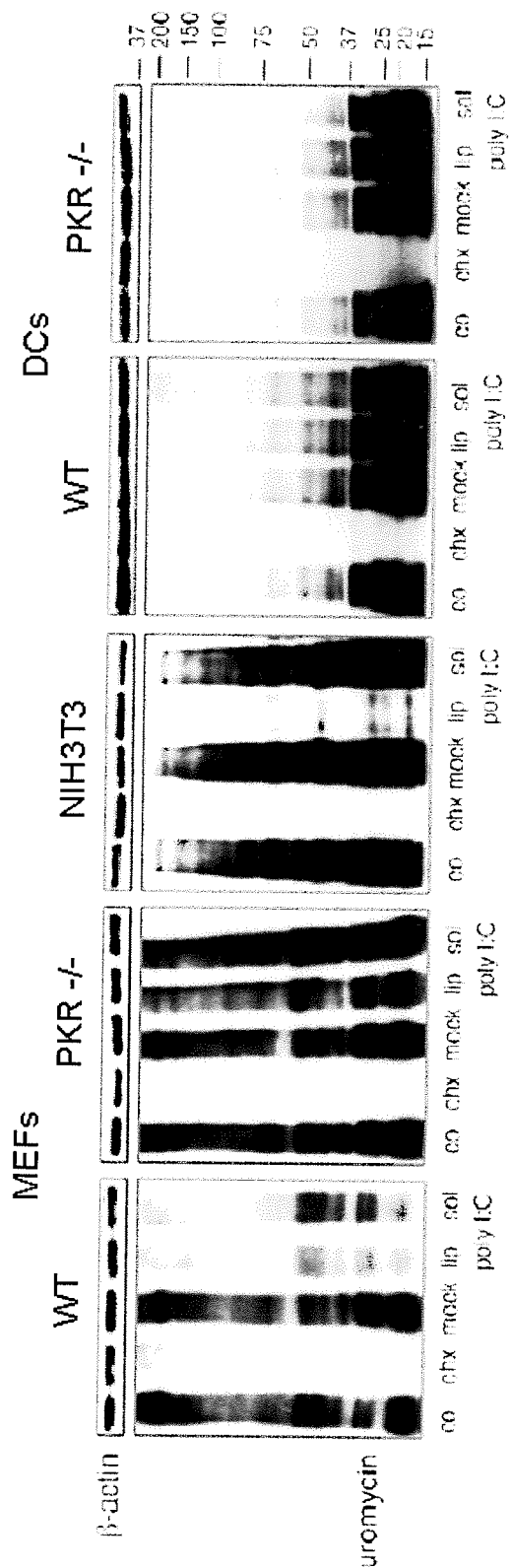
Figure 4A
Figure 4B
Figure 4C

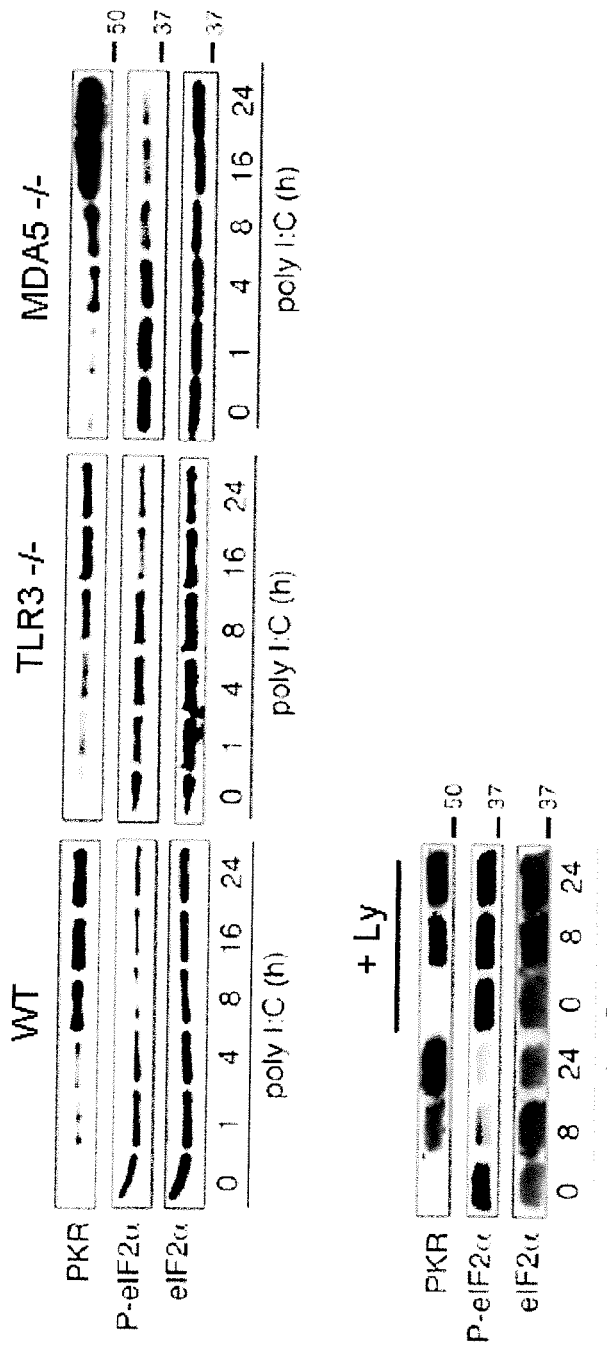
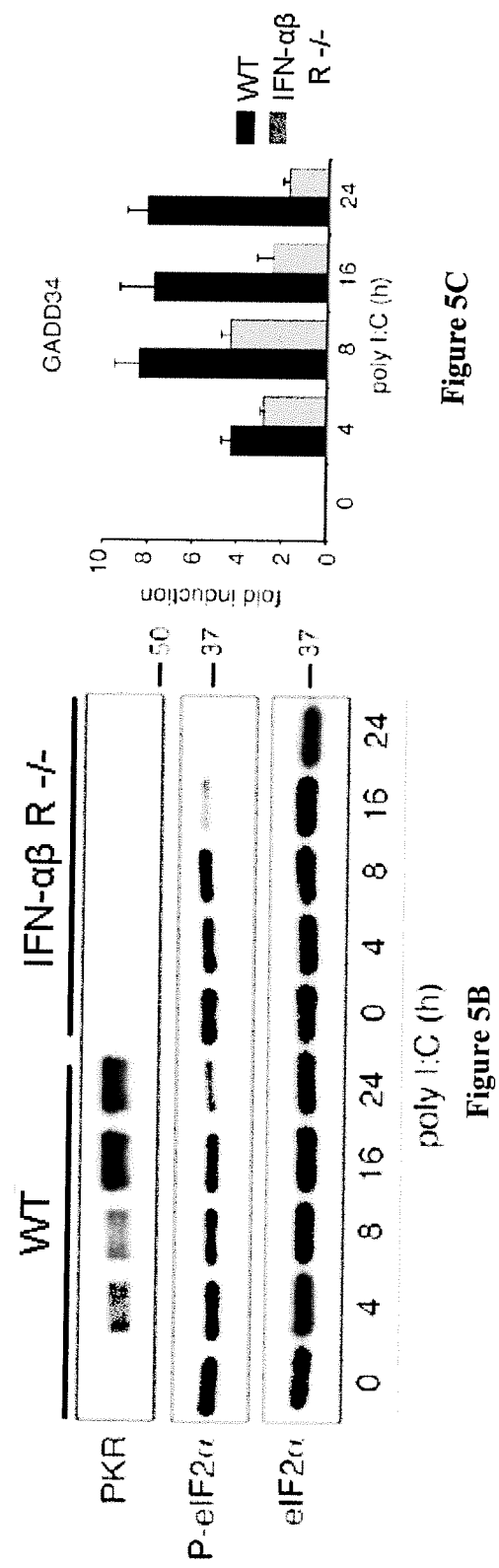
Figure 5A
Figure 5B
Figure 5C

INHIBITORS OF THE PP1/GADD34 COMPLEX FOR THE TREATMENT OF A CONDITION REQUIRING AN IMMUNOSUPPRESSIVE ACTIVITY

FIELD OF THE INVENTION

The present invention relates to the general field of the treatment and prevention of diseases involving an inflammatory condition, namely sepsis or infectious or viral diseases as well as diseases requiring for the of treatment an immunosuppressive activity namely autoimmune diseases and graft rejection.

BACKGROUND OF THE INVENTION

Dendritic cells (DCs) are regulators of the immune response whose antigen processing activities are controlled in response to pathogen-associated molecular patterns (PAMPS). DCs are most efficient at initiating antigen-specific responses, inducing differentiation of naive T cells. Upon stimulation via pattern recognition receptors, DCs begin a maturation process characterized by functional changes, such as cytokine production (e.g. IL-12) or upregulation of antigen presentation [Mellman, I. et al., 2001]. Double-stranded RNA (ds-RNA) present as viral genome or in virally infected cells is recognized by Toll-like receptor 3 (TLR3), which is expressed by several specialized cell types including DCs [Alexopoulou, L., et Al., 2001]. Upon stimulation with poly I:C, a dsRNA mimic, TLR3 triggers a complex signaling cascade leading to type I interferons (IFN) production [Alexopoulou, L., et Al., 2001 and Kawai, T. et Al., 2006]. In addition to membrane bound TLR3, another intracellular dsRNA receptor, the RNA helicase melanoma associated gene-5 (MDA5) induces type I IFN production in response to poly I:C via a different signaling cascade also leading to the nuclear translocation of IRF-3 and IRF-7 [Kawai, T. et Al., 2006 and Gitlin, L. et Al., 2006]. Once bound to their receptor on the cell surface, type I interferons activate the Janus tyrosine kinase/signal transducer and activator pathway, which induces the expression of a wide spectrum of cellular genes. Among these, there is the double-stranded RNA-dependent protein kinase (PKR), a key player of the interferon-mediated antiviral action, which is involved in cell differentiation and apoptosis [Donze, O. et al., 2004 and Scheuner, D. et al., 2006].

PKR is also activated by dsRNA in the cytosol and triggers translation initiation factor 2-alpha phosphorylation on serine 51 (eIF2-α) [Proud, C. G, 1995 and Williams, B. R., 1999] leading to protein synthesis shut-off and inhibition of viral replication. In addition to dsRNA detection, different stress signals trigger eIF2-α phosphorylation, thus attenuating mRNA translation and activating gene expression programs known globally as the integrated stress response (ISR) [Harding, H. P. et al., 2003]. To date, four kinases have been identified to mediate ISR: PKR, PERK (protein kinase RNA (PKR)-like ER kinase) [Harding, H. P., et al., 2000], GCN2 (general control non-derepressible-2) [Zhang, P. et al. 2002 and Berlanga, J. J. et al. 2006] and HRI (heme-regulated inhibitor) [Chen, J. J. et al., 1995 and Lu, L., et Al., 2001]. ER stress-mediated eIF2-α phosphorylation is carried out by PERK, which is activated by an excess of unfolded proteins accumulating in the ER lumen [Harding, H. P., et al., 2000]. Activated PERK phosphorylates eIF2-α, attenuating protein synthesis and triggering the translation of specific molecules such as the transcription factor ATF4, which is necessary to mount part of a particular ISR, known as the unfolded protein response (UPR) [Ron, D. & Walter, P., 2007 and Todd, D. J., et Al., 2008 and Zhang, K. & Kaufman. R. J. et Al., 2008].

Interestingly, dsRNA detection by TLR3, MDA5 and PKR is likely to occur concomitantly in cells like DCs, thus potentially resulting in conflicting signaling events and opposite biological effects (e.g. cellular activation v.s. translational arrest and/or anergy).

The inventors demonstrate here that poly I:C detection by DCs or fibroblasts activates the negative feedback control loop of the UPR and induces eIF2-α dephosphorylation through phosphatase 1 (PP1) and the expression of its inducible cofactor, the growth arrest and DNA damage-inducible protein 34 (GADD34/MyD116) [Connor, J. H., et Al., 2001]. As a consequence, the translational arrest, normally mediated through eIF2-α phosphorylation in response to cytosolic dsRNA detection, tapsigargin or tryptophan starvation, is prevented in activated DCs. This phenomenon allows DCs to perform their immune function, in conditions under which translation arrest would normally impair their activity. This point is illustrated by the demonstration that the absence of stress-induced translational inhibition in activated DCs is essential to produce normal amounts of interferon-β and to prevent caspase-3 cleavage and apoptosis and that DCs inactivated for the GADD34 gene are incapable of producing cytokines.

As is known, DCs play major role in inflammatory condition like autoimmune diseases by releasing inflammatory cytokines like interferon-β or IL-12. So, inhibiting GADD34 could allow controlling the overactive immune response in pathogenic condition like autoimmune diseases or graft rejection by blocking the release of inflammatory cytokines released by DCs or other cells.

As of today, very few treatments are available for the treatment of autoimmune diseases or graft rejection, that have an acceptable safety index.

Thus, there is a permanent need in the art for new molecules for the treatment of autoimmune diseases or graft rejection.

SUMMARY OF THE INVENTION

The invention is based on the discovery that GADD34 represents a novel and promising target controlling inflammation by blocking the release of inflammatory cytokines and other secreted molecular mediators leading to pathogenic conditions such as autoimmune diseases or infectious and non-infectious diseases leading to hypercytokinemia including graft versus host disease (GVHD), acute respiratory distress syndrome (ARDS), sepsis, avian influenza, smallpox, and systemic inflammatory response syndrome (SIRS). Inhibitors of GADD34 are already known for the treatment of cancer like carcinoma or sarcoma (see for example WO 2008028965).

Thus, the invention relates to an inhibitor of the activity or the formation of the PP1/GADD34 complex for the treatment of a condition requiring an immunosuppressive activity or an anti-inflammatory activity.

In one aspect, the invention relates to an inhibitor according to the invention for the treatment of autoimmune diseases or inflammatory conditions.

In a second aspect, the invention relates to an inhibitor according to the invention for the treatment of graft rejection.

DETAILED DESCRIPTION OF THE INVENTION

Definitions

As used herein, the term "dendritic cells (DCs)" denotes immune cells that form part of the mammalian immune system. Their main function is to process antigen material and present it on the surface to other cells of the immune system, thus functioning as antigen-presenting cells.

As used herein, the term "autoimmune diseases" denotes an overactive immune response of the body against substances and tissues normally present in the body. In other words, the body really attacks its own cells. This may be restricted to certain organs (e.g. in thyroiditis) or involve a particular tissue in different places (e.g. Goodpasture's disease which may affect the basement membrane in both the lung and the kidney). The treatment of autoimmune diseases is typically with immunosuppression-medication which decreases the immune response.

As used herein, the term "Poly I:C" (polyinosinic:polycytidylic acid or polyinosinic-polycytidylic acid sodium salt) denotes an immunostimulant. It is used to simulate viral infections. Poly I:C is known to interact with toll-like receptor (TLR) 3, which is expressed in the intracellular compartments of B-cells and dendritic cells. Poly I:C is structurally similar to double-stranded RNA, which is present in some viruses and is a "natural" stimulant of TLR3.

Thus, Poly I:C can be considered a synthetic analog of double-stranded RNA and is a common tool for scientific research on the immune system.

As used herein, the term "GADD34" for "DNA damage-inducible protein 34" or MyD116 denotes a protein inhibitor 1 (I-1) interacting protein that associates with the C terminus of human I-1. GADD34, whose expression in mammalian cells is elevated by growth arrest, DNA damage, and other forms of cell stress, has structural homology to a region of the herpes simplex virus (HSV-1) neurovirulence factor ICP-345, previously shown to bind PP1. An exemplary sequence for human GADD34 gene (PPP1R15A) is deposited in the database NCBI under accession number NW 927240.1 and mRNA U83981.1.

As used herein, the term "an inhibitor of the formation of the PP1/GADD34 complex" denotes an inhibitor able to compete in the µM range with GADD34 to form a complex with PP1 and thereby render said complex non functional, or to block GADD34 expression or to render GADD34 structurally inactive. In another term, "an inhibitor of the formation of the PP1/GADD34 complex" will have an $EC_{50}$ not greater than 50 µM and preferably not greater than 25 µM.

As used herein, the term "an inhibitor of the activity of the PP1/GADD34 complex" denotes an inhibitor in the µM range that is responsible for the non expression of said complex in the cell and/or for the non induction of a reaction of the immune system or for a decreased reaction of the immune system compared with its reaction in the absence of said inhibitor. In another term, "an inhibitor of the activity of the PP1/GADD34 complex" will have an EC50 not greater than 50 µM and preferably not greater than 25 µM.

As used herein, the term 'selective inhibitor' denotes a compound which just inhibit GADD34 activity or expression, without affecting the activity of the non inducible PP1 activator CReP or PP1 activity outside of the GADD34 complex.

As used herein, the term "protein phosphatase 1 (PP1)" denotes a major eukaryotic protein serine/threonine phosphatase that regulates an enormous variety of cellular functions through the interaction of its catalytic subunit (PP1c) with over fifty different established or putative regulatory subunits.

As used herein, the term "graft" denotes a cell, tissue, organ or otherwise any biological compatible lattice for transplantation.

As used herein, the term "graft rejection" denotes acute or chronic rejection of cells, tissue or solid organ allo- or xenografts of e.g. pancreatic islets, stem cells, bone marrow, skin, muscle, corneal tissue, neuronal tissue, heart, lung, combined heart-lung, kidney, liver, bowel, pancreas, trachea or oesophagus, or graft-versus-host diseases.

As used herein, the term "allogeneic" denotes a graft derived from a different animal of the same species.

As used herein, the term "xenogeneic" denotes a graft derived from an animal of a different species.

As used herein, the term "transplant" denotes a biocompatible lattice or a donor tissue, organ or cell, to be transplanted. An example of a transplant may include but is not limited to skin, bone marrow, and solid organs such as heart, pancreas, kidney, lung and liver.

As used herein, the terms "treating" or "treatment", denotes reversing, alleviating, inhibiting the progress of, or preventing the disorder or condition to which such term applies, or one or more symptoms of such a disorder or condition.

Inhibitors and Uses Thereof

A first aspect of the invention relates to an inhibitor of the activity or the formation of the PP1/GADD34 complex for the treatment of a condition requiring an immunosuppressive activity or an anti-inflammatory activity.

In a first embodiment the inhibitor according to the invention is useful for the treatment of autoimmune diseases.

The inhibitor may be useful for the treatment of autoimmune diseases including, but not limited to systemic lupus erythematosus, arthritis, Sjögren's syndrome, psoriasis, dermatitis herpetiformis, vitiligo, mycosis fungoides, allergic contact dermatitis, atopic dermatitis, *lichen planus, Pityriasis lichenoides* and *varioliforms acuta* (PLEVA), catastrophic antiphospholipid syndrome.

In a second embodiment, the inhibitor according to the invention is useful for the treatment of inflammatory conditions.

As used herein, the term "inflammatory condition(s)" denotes a biological response characterized by cellular and biochemical components. For example, the cellular component is characterized by leukocyte migration (swelling) and the biochemical component is characterized by activation of the complement system or by the production of mediators, chemokines and cytokines.

The inhibitor may be useful for the treatment of inflammatory conditions including, but not limited to allergy, asthma, Myopathies, cancer, acute respiratory distress syndrome (ARDS), sepsis, and systemic inflammatory response syndrome (SIRS), Inflamatory bowel diseases, psoriasis.

In another preferred embodiment, the inflammatory condition is sepsis.

In another embodiment, the inhibitor according to the invention may be useful for the treatment of inflammatory conditions caused by an infectious or viral disease or any disease leading to aggravated conditions due to an hyper-production of inflammatory mediators or cytokine storms.

In a preferred embodiment, inflammatory conditions caused by an infectious or viral disease may be Chikungunya virus infection, influenza infection, herpes infection avian influenza, Smallpox, severe acute respiratory syndrome (SARS).

In a most preferred embodiment, the viral disease is caused by a Chikungunya virus infection.

In a third embodiment, the inhibitor according to the invention is useful for the treatment of graft rejection or graft versus host disease (GVHD).

In a preferred embodiment, the graft rejection concerns an allogeneic or a xenogeneic transplant.

In another preferred embodiment, the inhibitor according to the invention is an inhibitor of GADD34.

In another preferred embodiment, the inhibitor according to the invention is an inhibitor of PP1 in complex with GADD34.

In another preferred embodiment, the inhibitor according to the invention inhibits the interaction domain comprised between amino acids residues 540 and 600 of GADD34.

In a preferred embodiment, the inhibitor according to the invention is selected from salubrinal, tautomycine and calyculin A.

In another preferred embodiment, the inhibitor according to the invention is a peptide consisting of or comprising a fragment of GADD34.

In another embodiment, the inhibitor according to the invention is a selective inhibitor of GADD34. A selective inhibitor according to the invention may be found in the patent application WO2008028965.

In a preferred embodiment, the selective inhibitor is selected from small inactivating RNAs or other compounds capable of blocking the expression of GADD34 at the transcription or translational level.

In one embodiment, inhibitor of the invention may be a low molecular weight inhibitor, e.g. a small organic molecule (natural or not).

The term "small organic molecule" refers to a molecule (natural or not) of a size comparable to those organic molecules generally used in pharmaceuticals. The term excludes biological macromolecules (e.g., proteins, nucleic acids, etc.). Preferred small organic molecules range in size up to about 5000 Da, more preferably up to 2000 Da, and most preferably up to about 1000 Da.

In another embodiment, inhibitor of the invention may consist in an antibody which inhibits the activity or the formation of the PP1/GADD34 complex or an antibody fragment which inhibits the activity or the formation of the PP1/GADD34 complex.

Antibodies directed against the PP1/GADD34 complex can be raised according to known methods by administering the appropriate antigen or epitope to a host animal selected, e.g., from pigs, cows, horses, rabbits, goats, sheep, and mice, among others. Various adjuvants known in the art can be used to enhance antibody production. Although antibodies useful in practicing the invention can be polyclonal, monoclonal antibodies are preferred. Monoclonal antibodies against the PP1/GADD34 complex can be prepared and isolated using any technique that provides for the production of antibody molecules by continuous cell lines in culture. Techniques for production and isolation include but are not limited to the hybridoma technique originally described by Kohler and Milstein (1975); the human B-cell hybridoma technique (Cote et al., 1983); and the EBV-hybridoma technique (Cole et al. 1985). Alternatively, techniques described for the production of single chain antibodies (see, e.g., U.S. Pat. No. 4,946,778) can be adapted to produce anti-GADD34/PP1 complex single chain antibodies. PP1/GADD34 complex inhibitor useful in practicing the present invention also include anti-PP1/GADD34 complex antibody fragments including but not limited to F(ab')$_2$ fragments, which can be generated by pepsin digestion of an intact antibody molecule, and Fab fragments, which can be generated by reducing the disulfide bridges of the F(ab')$_2$ fragments. Alternatively, Fab and/or scFv expression libraries can be constructed to allow rapid identification of fragments having the desired specificity to the PP1/GADD34 complex.

Humanized anti-PP1/GADD34 complex antibodies and antibody fragments thereof may also be prepared according to known techniques. "Humanized antibodies" are forms of non-human (e.g., rodent) chimeric antibodies that contain minimal sequence derived from non-human immunoglobulin. For the most part, humanized antibodies are human immunoglobulins (recipient antibody) in which residues from a hypervariable region (CDRs) of the recipient are replaced by residues from a hypervariable region of a non-human species (donor antibody) such as mouse, rat, rabbit or nonhuman primate having the desired specificity, affinity and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. Methods for making humanized antibodies are described, for example, by Winter (U.S. Pat. No. 5,225,539) and Boss (Celltech, U.S. Pat. No. 4,816,397).

In still another embodiment, PP1/GADD34 complex inhibitor may be selected from aptamers. Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. and Gold L., 1990. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., 1999. Peptide aptamers consists of a conformationally constrained antibody variable region displayed by a platform protein, such as *E. coli* Thioredoxin A that are selected from combinatorial libraries by two hybrid methods (Colas et al., 1996).

Therapeutic Composition

Another object of the invention relates to a therapeutic composition comprising an inhibitor according to the invention for the treatment of a condition requiring an immunosuppressive activity.

Any therapeutic agent of the invention may be combined with pharmaceutically acceptable excipients, and optionally sustained-release matrices, such as biodegradable polymers, to form therapeutic compositions.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

The form of the pharmaceutical compositions, the route of administration, the dosage and the regimen naturally depend upon the condition to be treated, the severity of the illness, the age, weight, and sex of the patient, etc.

The pharmaceutical compositions of the invention can be formulated for a topical, oral, intranasal, parenteral, intraocular, intravenous, intramuscular or subcutaneous administration and the like.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The doses used for the administration can be adapted as a function of various parameters, and in particular as a function of the mode of administration used, of the relevant pathology, or alternatively of the desired duration of treatment.

In addition, other pharmaceutically acceptable forms include, e.g. tablets or other solids for oral administration; time release capsules; and any other form currently can be used.

Alternatively, compounds of the invention which inhibit the activity or the formation of the PP1/GADD34 complex can be further identified by screening methods as hereinafter described.

Screening Methods

Another object of the invention relates to a method for screening a compound which inhibits the activity or the formation of the PP1/GADD34 complex.

In particular, the invention provides a method for screening an inhibitor of the PP1/GADD34 complex for the treatment of different disorder.

For example, the screening method may measure the binding of a candidate compound to PP1/GADD34 complex, or to cells or membranes bearing PP1/GADD34 complex or a fusion protein thereof by means of a label directly or indirectly associated with the candidate compound. Alternatively, a screening method may involve measuring or, qualitatively or quantitatively, detecting the competition of binding of a candidate compound to the receptor with a labelled competitor (e.g., antagonist).

In a particular embodiment, the screening method of the invention comprises the step consisting of:
  a) providing a plurality of cells expressing the PP1/GADD34 complex;
  b) incubating said cells with a candidate compound;
  c) determining whether said candidate compound binds to PP1/GADD34 complex; and
  d) selecting the candidate compound that inhibits the PP1/GADD34 complex.

A test for screening inhibitors according to the invention can be found in Boyce, M. et al., 2005 and Novoa, I. et al., 2001.

Several methods can be use to screen for such inhibitor:
  1: In vitro using eIF-2 phosphorylation detection with specific antibodies (WB or ELISA) in rabbit reticulocyte lysate.
  2: A screening method using recombinant GADD34 and PP1 followed by size exclusion chromatography to follow the disruption of the complex in presence of potential inhibitors.
  3: A functional assay in which cytokine production is monitored in activated DCs upon exposure to the inhibitor. Intracellular FACS scan or ELISA can be used to detect cytokine production in multiwell plates.
  4: Rapid and complete translational arrest in response to tunicamycin in presence of potential inhibitors. Detection of translation can be performed by FACS using the SUnSET technology (Schmidt et al. Nature Methods 2009).

In general, such screening methods involve providing appropriate cells which express the PP1/GADD34 complex, its orthologs and derivatives thereof on their surface. In particular, a nucleic acid encoding the PP1/GADD34 complex may be employed to transfect cells to thereby express the PP1/GADD34 complex. Such a transfection may be achieved by methods well known in the art.

In a particular embodiment, cells are selected from the group consisting dendritic cells (DCs) and other immune cells involved in cytokine and inflammatory mediator release including but not limited to macrophages, T cells, neutrophiles, mastocytes.

The screening method of the invention may be employed for determining an inhibitor by contacting such cells with compounds to be screened and determining whether such compound inhibit or not the PP1/GADD34 complex.

According to a one embodiment of the invention, the candidate compound may be selected from a library of compounds previously synthesised, or a library of compounds for which the structure is determined in a database, or from a library of compounds that have been synthesised de novo or natural compounds.

The candidate compound may be selected from the group of (a) proteins or peptides, (b) nucleic acids and (c) organic or chemical compounds (natural or not). Illustratively, libraries of pre-selected candidate nucleic acids may be obtained by performing the SELEX method as described in documents U.S. Pat. Nos. 5,475,096 and 5,270,163. Further illustratively, the candidate compound may be selected from the group of antibodies directed against the PP1/GADD34 complex.

Such the method may be used to screen PP1/GADD34 complex inhibitor according to the invention.

The invention will be further illustrated by the following figures and examples. However, these examples and figures should not be interpreted in any way as limiting the scope of the present invention.

FIGURES

FIG. 1A-E. Transcription factors ATF4 and CHOP are induced in DCs upon poly I:C stimulation. a) ATF4 mRNA expression was measured by quantitative PCR (qPCR) in response to poly I:C stimulation at different time points (left panel). ATF4 protein levels were quantified in nuclear extract of poly I:C-stimulated DCs by immunoblot. Protein levels were increased after 8 h of stimulation, similarly to cells treated with tunicamycin. (right panel). Mock was treated with DMSO, in which tunicamycin was dissolved; immunoblot for histone H1 is shown as equal loading control. b) CHOP mRNA expression was found by qPCR to be increased by 8 folds in poly I:C-activated DCs. c) Phosphatase 1 (PP1) mRNA expression levels were only modestly increased by poly I:C. d) GADD34 mRNA expression was increased up to 14 folds (top panel). A treatment with the proteasome inhibitor MG132 (2 µM, added 4 h before harvesting) was necessary to allow GADD34 detection by immunoblot. GADD34 accumulates in the cells after 8 h of poly I:C stimulation, in comparable amounts to those induced by tunicamycin. e) CReP (constitutive PP1 cofactor) mRNA expression levels were very modestly induced.

FIG. 2A-D. Protein synthesis and eIF2-α dephosphorylation are tightly regulated during poly I:C induced DC maturation. a) Protein synthesis was quantified in poly I:C activated DCs using puromycin labelling followed by immunoblot with the anti-puromycin mAb 12D10. Protein synthesis was enhanced in the first hours of poly I:C stimulation, followed by a reduction after 8 h. Controls are cells non treated with puromycin (co) and cells treated with cycloheximide (chx) 5' min before puromycin incorporation. β-actin immunoblot is shown for equal loading control. b) Immunoblot for phosphorylated (P-eIF2-α) and total eIF2-α were performed on the same DC extracts. Quantification of P-eIF2-α levels is also shown. c) DCs were activated with soluble poly I:C for 24 h and treated with 75 µM salubrinal (specific inhibitor of the PP1-GADD34 complex) for the last 4 h of stimulation, prior detection of P-eIF2-α a by immunoblot. d) Identical experiments performed with tautomycin, a different PP1 inhibitor.

FIG. 3A-D. PKR phosphorylates eIF2-α in activated DCs. a) Wild-type and PKR$^{-/-}$ were stimulated with soluble poly I:C for different time and PKR and P-eIF2-α were detected by immunoblot. Levels of PKR are strongly increased upon maturation. PKR levels are inversely correlated with the intensity of P-eIF2-α, which is gradually reduced. In non-activated PKR$^{-/-}$ DCs levels of P-eIF2-α are comparable to wild-type DCs, while upon poly I:C stimulation P-eIF2-α is nearly abolished. b) A comparable decrease of P-eIF2-α following poly I:C stimulation (sol) in PKR$^{-/-}$ DCs was observed upon direct delivery of poly I:C in the cytosol (lip). A control with sodium arsenite-treated cells (500 µM, 30') was performed. c) Lipofection of poly I:C (lip) and not soluble poly I:C (sol) induces PKR-dependent eIF2-α phosphorylation in wild-type MEFs and NIH3T3 cells. d) NIH3T3 cells were lipofected with poly I:C for 8 h, with the addition of the proteasome inhibitor MG132 in the last 4 h of treatment. In contrast to DCs (FIG. 1d) GADD34 levels are decreased. β-actin immunoblot is shown as an equal loading control.

FIG. 4A-C. DCs are protected from the inhibition of translation induced by PKR upon cytosolic poly I:C sensing. a) Monitoring of translation in wild-type and PKR$^{-/-}$ MEFs, DCs and NIH3T3 treated with soluble (sol) or lipofected poly I:C (lip) for 8 h. Lipofection of poly I:C in MEFs (wt) and NIH3T3 induces PKR-dependent translation arrest. Soluble poly I:C does not affect NIH3T3 cells, but inhibits translation in wt MEFs. In contrast, translational arrest by poly I:C treatment is never observed in DCs. Controls with no puromycin (co), cycloheximide (chx) and lipofectamine alone (mock) are presented. β-actin immunoblot is shown for equal loading control. b) NIH3T3, MEFs and DCs were treated for 8 h with lipofected Cy5 labelled-poly I:C prior monitoring by FACS. One representative experiment of three is presented. c) Translation was monitored in DCs stimulated for 4 or 8 h with poly I:C. Protein synthesis was strongly reduced in presence of salubrinal (added to the cells 2 h before poly I:C stimulation).

FIG. 5A-C. Signal transduction pathways involved in eIF2-α phosphorylation regulation and GADD34 transcription. a) Wild-type, TLR3$^{-/-}$ and MDA5$^{-/-}$ DCs were stimulated with poly I:C for different time prior immunoblotting for P-eIF2-α., eIF2-α, and PKR. In all cells types, PKR levels are increased during DC maturation, while eIF2-α. is dephosphorylated (top panel). In contrast, treatment with the PI3 kinase inhibitor Ly294002 (Ly) (1 h before harvesting) efficiently prevents eIF2-α. dephosphorylation (bottom panel). b) No change in eIF2-α. dephosphorylation is observed in IFN-αβ R$^{-/-}$ DCs stimulated with poly I:C, while the levels of PKR are drastically reduced in these cells. c) qPCR monitoring of GADD34 mRNA levels in wild-type and IFN-αβ R$^{-/-}$ activated DCs. Levels are reduced by to 2 to 6 folds in the IFN-αβ R$^{-/-}$ compared to wt cells.

Figure 6A:
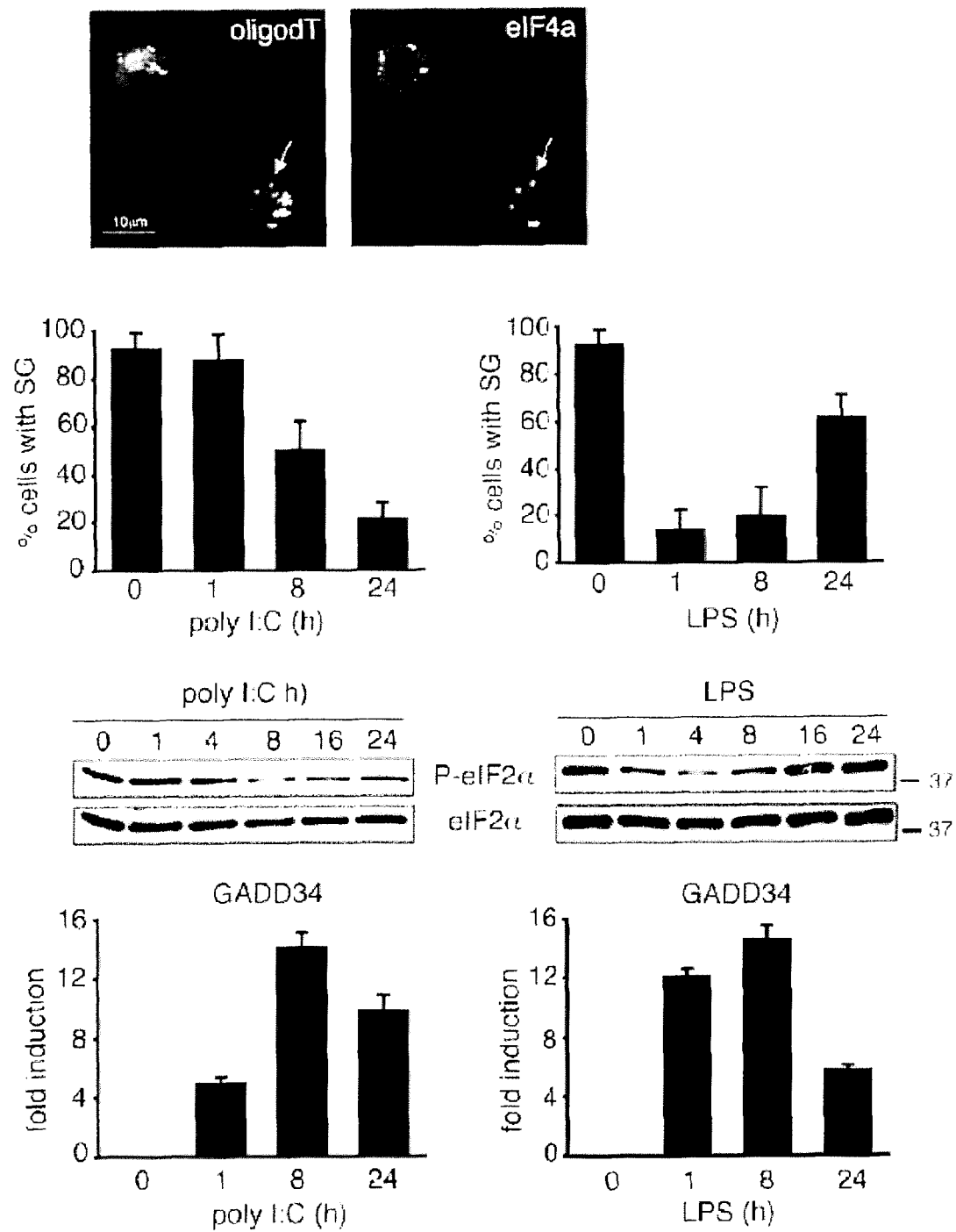
Figure 6B:
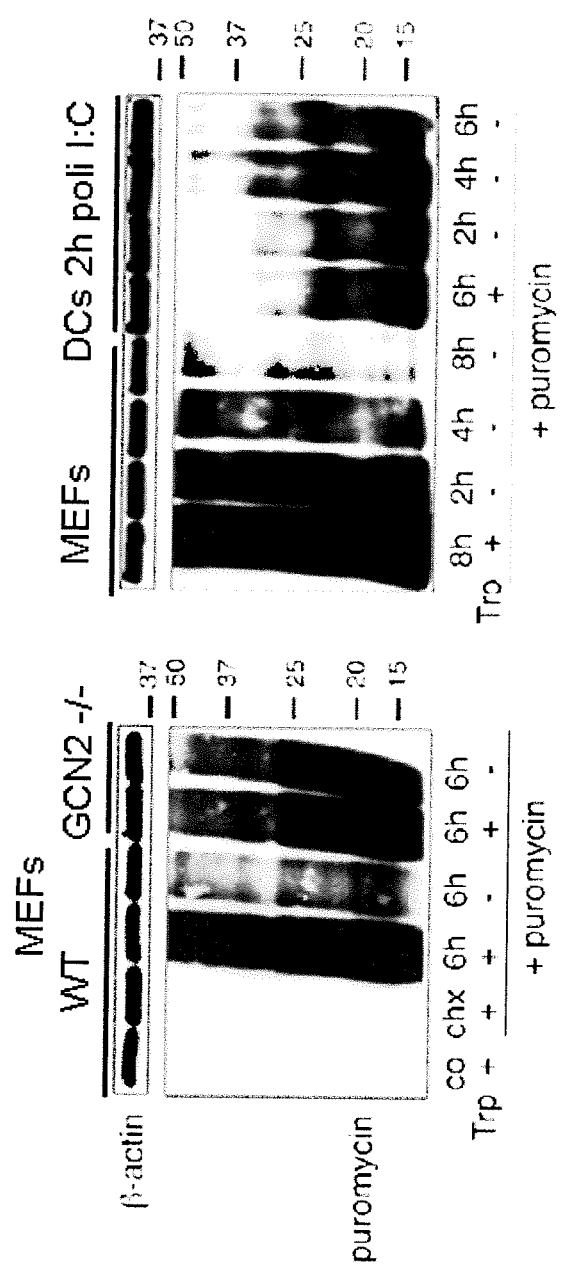
Figure 6B:
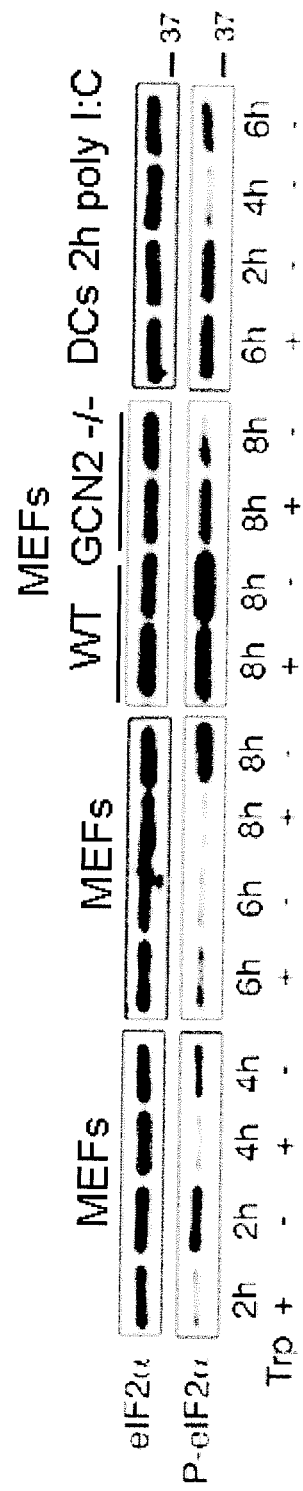

FIG. 6A-B. Activated DCs are resistant to stress granules formation and tryptophan starvation. a) DCs were activated with poly I:C or LPS for different time and treated with 500 µM sodium arsenite for the last 30' of each time point. Stress granules (SG) formation was visualised by confocal microscopy after mRNA in situ hybridization with oligodT and staining with eIF4A antibody. Bar, 10 µm. (top panel). The number of DCs bearing SGs was plotted against the time of maturation. SGs are found in almost 100% of non-activated DCs, a proportion, which is reduced upon activation. Kinetics of SG formation corresponds to the state of eIF2-α phosphorylation and GADD34 expression induced by poly I:C or LPS (bottom panel). b) Translational intensity was measured in wild-type and GCN2$^{-/-}$ MEFs grown in complete or tryptophan (Trp)-free medium for 6 h. Translation is inhibited in response to tryptophan depletion in wt but not in GCN2$^{-/-}$ MEFs. (top left panel). DCs, activated with poly I:C for 2 h, are then starved for 6 h (poly I:C was kept during starvation). Contrary to MEFs, activated DCs exposed to tryptophan depletion, do not display any inhibition of translation for at least 6 h. (top right panel). Controls with no puromycin and cycloheximide (chx) are shown. β-actin immunoblots are presented as equal loading control. P-eIF2-α. and eIF2-α. were also monitored in wt and GCN2$^{-/-}$ MEFs and DCs. eIF2-α phosphorylation in response to tryptophan depletion is observed in wt MEFs but not in GCN$^{-/-}$ MEFs or DCs (bottom panel).

Figure 7A:
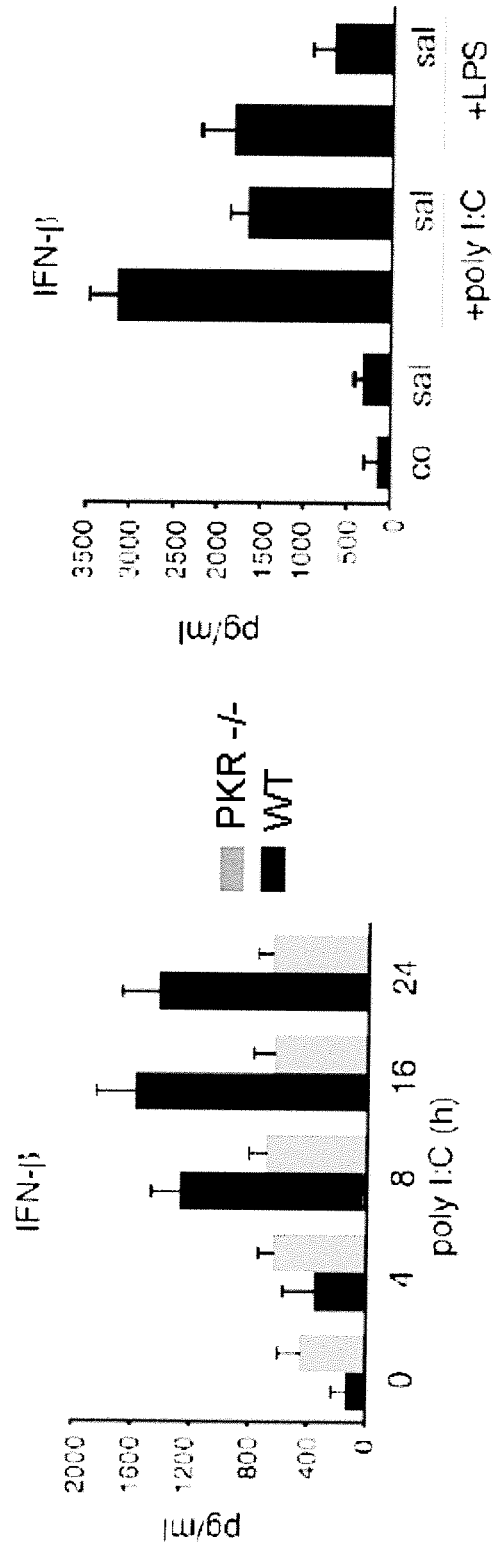
Figure 7B:
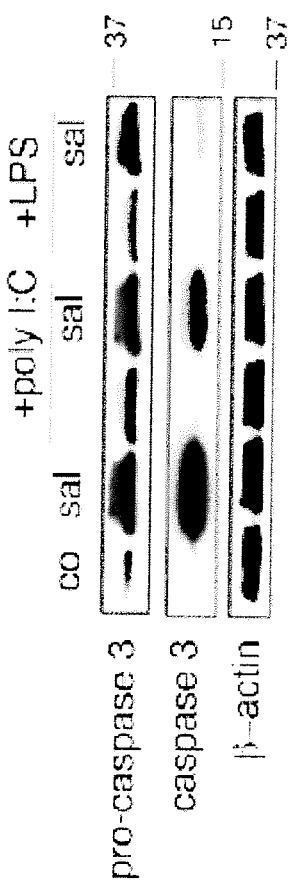

FIG. 7A-B. eIF2-α dephosphorylation is essential for normal IFN-β production and caspase-3 inhibition in DCs. a) IFN-β was quantified by ELISA in wild-type and PKR$^{-/-}$ bmDCs stimulated with poly I:C for different time. The production of IFN-β in the PKR$^{-/-}$ is significantly reduced compared to wt cells, thus confirming the requirement of PKR for this process (left panel). IFN-β was quantified in DCs stimulated with poly I:C or LPS for 8 h, in presence or absence of the GADD34/PP1 inhibitor salubrinal (added 2 h before stimulation) (right panel). Upon salubrinal treatment, IFN-β secretion in activated DCs is drastically reduced, indicating that the control of eIF2-α phosphorylation during PKR activation is essential for normal IFN-β production. b) Caspase 3 cleavage was revealed by immunoblot in DCs stimulated with poly I:C or LPS for 8 h, in presence or absence of salubrinal (added 2 h before stimulation). Salubrinal treatment alone induces a massive increase in total levels of caspase-3 (visualised as a band at 35 kDa) and its cleaved active form (17 kDa). Treatments with poly I:C or LPS decrease caspase-3 expression and the cleavage induced by salubrinal alone, probably due to GADD34 induction in activated DCs. β-actin immunoblot is shown as an equal loading control.

Figure 8:
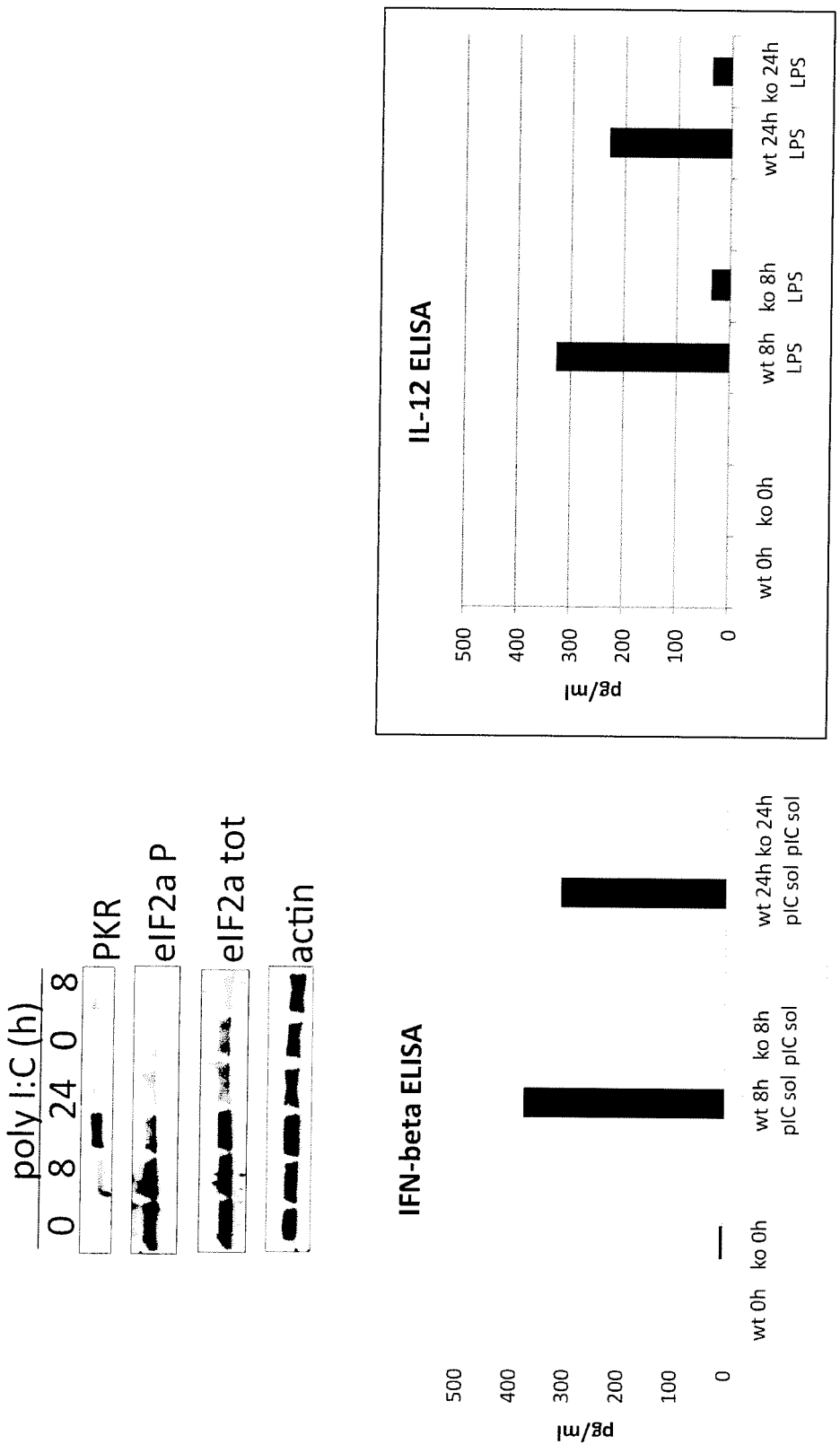

FIG. 8. activated DCs deficient for GADD34 are incapable of producing IFN-β and IL-12.

Wild-type and GADD34$^{-/-}$ DCs were stimulated with poly I:C for different time prior immunoblotting for P-eIF2-α., eIF2-α, and PKR. In all cells types, PKR levels are strongly decreased during DC maturation, while eIF2-α. is strongly reduced and phosphorylated (top panel). IFN-β and IL-12 was quantified by ELISA in wild-type and GADD34$^{-/-}$ bmDCs stimulated with poly I:C or LPS for different time. The production of IFN-β and IL-12 in the GADD34$^{-/-}$ is significantly reduced compared to wt cells, thus confirming the requirement of GADD34 for this process and explaining the poor expression of PKR in these cells (PKR is IFN inducible).

Figure 9A:
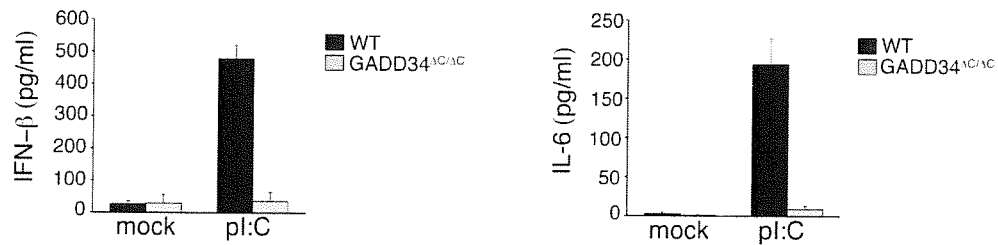
Figure 9:
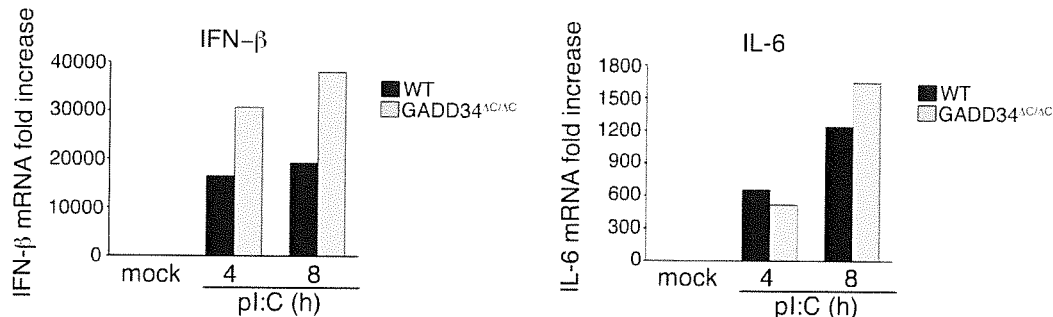
Figure 9C:
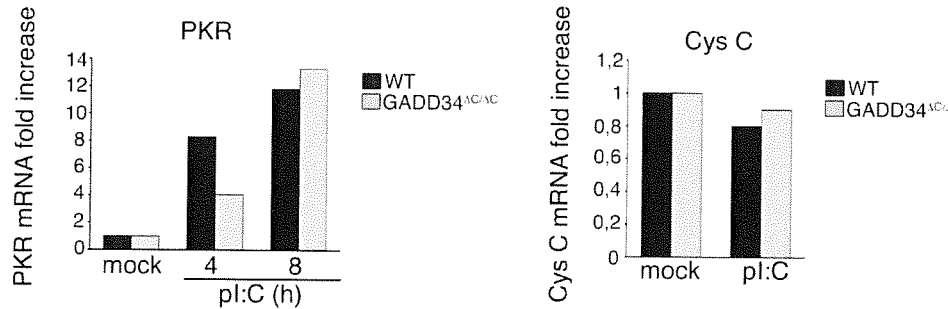
Figure 9C:
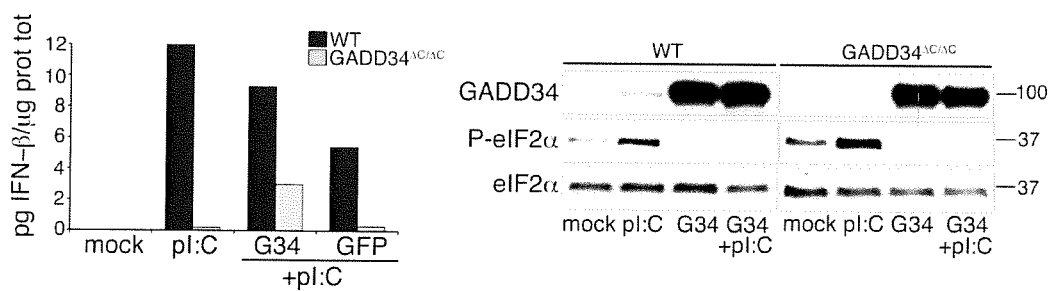

FIG. 9A-C: GADD34 is required for cytokine (IFN-β and IL-6) production by poly I:C-stimulated MEFs.

A) After 6 h of poly I:C stimulation, IFN-β (left panel) and IL-6 (right panel) in cell culture supernatants of wild-type and GADD34$^{\Delta C/\Delta C}$ MEFs were quantified by ELISA. Mock are samples treated with lipofectamine alone. Data are mean±SD of five (IFN-β) and three (IL-6) independent experiments. B) Wild-type and GADD34$^{\Delta C/\Delta C}$ MEFs were treated with poly I:C for the indicated times, total RNA was extracted and quantitative PCR were performed on cDNA. Fold increase of the indicated transcripts was calculated compared to a value=1 for each of the mock samples (treated with lipofectamine only). IFN-β, IL-6 and PKR transcripts were upregulated upon poly I:C stimulation in both wild-type and GADD34$^{\Delta C/\Delta C}$ MEFs and, at late time points, even more in GADD34$^{\Delta C/\Delta C}$ MEFs than in wild-type. Level of Cystatin C transcript remained approximately constant upon poly I:C treatment in both wild-type and GADD34$^{\Delta C/\Delta c}$ MEFs. Data are representative of two independent experiments with similar results. C) Wild-type and GADD34$^{\Delta C/\Delta c}$ MEFs were transfected overnight with a plasmid carrying the murine sequence of GADD34 and then treated with poly I:C for 6 h. IFN-β production was quantified by ELISA in cell culture supernatants (left panel), while effective eIF2α dephosphorylation was checked by immunoblot (right panel). One of three independent experiments with similar results is shown.

Figure 10A:
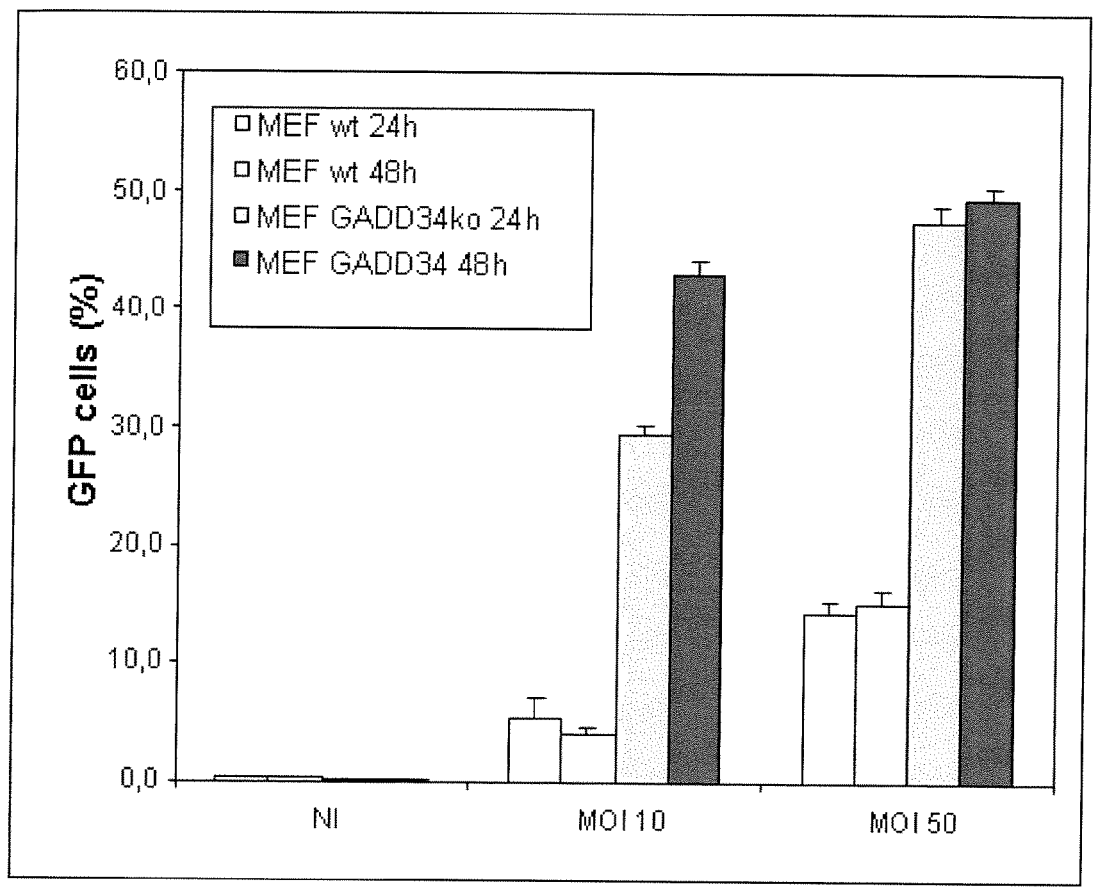
Figure 10B:
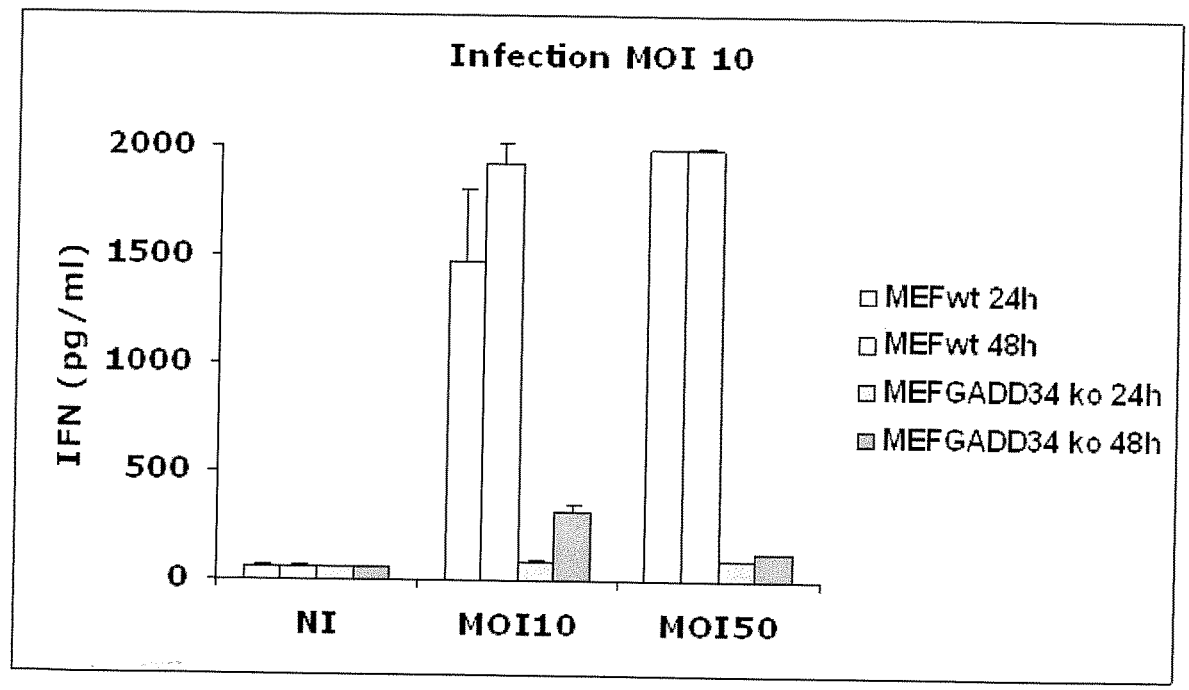

FIG. 10A-C. CHIKV infection and IFN-β production are controlled by GADD34 in MEFs.

A) Wild-type and GADD34$^{\Delta C/\Delta C}$ MEFs were exposed to 10 or 50 MOI of CHIKV for 24 h or 48 h and productive infection was estimated by GFP expression. B) IFN-β production by wild-type and GADD34$^{\Delta C/\Delta C}$ MEFs exposed to CHIKV was quantified by ELISA in cell culture supernatants. C) Murine IFN-β was added 3 h before infection of wild-type and GADD34$^{\Delta C/\Delta C}$ MEFs with CHIKV (10 MOI). Productive infection was estimated by GFP expression 24 h after CHIKV exposure. Data represented in A, B and C mean±SD of triplicates. One of two independent results with similar results is shown.

Figure 11:
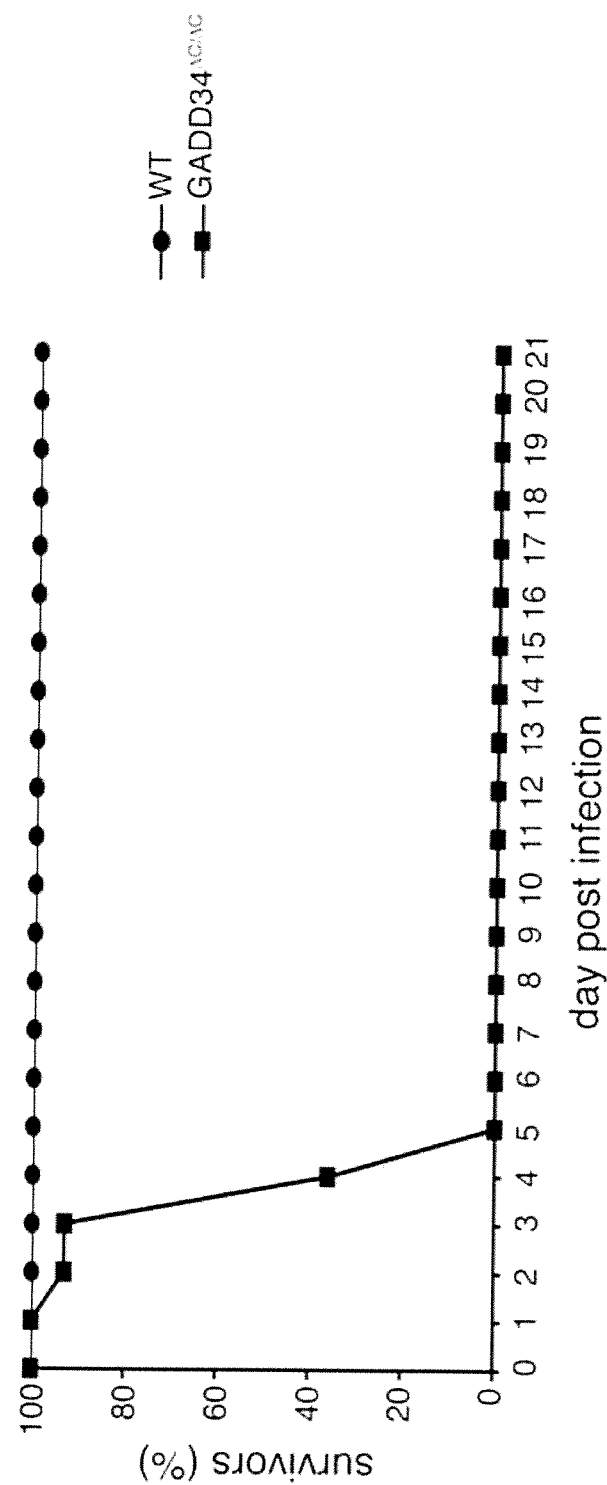

FIG. 11. CHIKV infection in mouse neonates.

Wild-type (FVB) and GADD34$^{\Delta C/\Delta C}$ mouse neonates (12-day-old) were inoculated intradermally with $10^6$ PFU of CHIKV and observed for lethality (n=14 per group).

EXAMPLE 1

Material & Methods
Mice

Male C57BL/6 mice 6 week-old were purchased from Charles River Laboratories. TLR-3$^{-/-}$ mice were obtained from L. Alexopoulou (CIML, Marseille), IFN-α/β R$^{-/-}$ mice from M. Dalod (CIML, Marseille), MDA-5$^{-/-}$ mouse bone marrow from M. Colonna (Washington University) and PKR$^{-/-}$ mouse bone marrow from Caetano Reis e Sousa (Cancer Research UK, London).

Cell Culture

Bone marrow-derived DCs were obtained and cultured as described previously[50]. NIH3T3 cells were cultured in RPMI 1640 (GIBCO) supplemented with 10% FCS (HyClone, PERBIO), 100 units/ml penicillin and 100 µg/ml streptomycin (GIBCO). Wild-type and PKR$^{-/-}$ MEFs (from Caetano Reis e Sousa) were cultured in DMEM, 10% FCS, pen/strep. Wild-type and GCN2$^{-/-}$ MEFs (from David Ron) were cultured in RPMI, 10% FCS, pen/strep, MEM non-essential amino acids (GIBCO), 55 µM beta-mercaptoethanol. For the tryptophan starvation experiments, MEFs and DCs were cultured for the indicated time in RPMI 1640 Tryptophan—medium (21875, GIBCO). All cells were cultured at 37° C. and 5% $CO_2$.

Chemicals

MEFs, NIH3T3 and immature DCs were treated for the indicated time with 10 µg/ml poly I:C (InvivoGen), alone or in combination with lipofectamine 2000 (Invitrogen). 2 µg/ml tunicamycin (SIGMA) was added to DCs for 2 h; 2 µM MG132 (BIOMOL International) was added to DCs and NIH3T3 4 h before harvesting; 75 µM salubrinal (Calbiochem) or 100 nM tautomycin (Calbiochem) were added to DCs 4 h before harvesting; 500 µM sodium arsenite (SIGMA) was added for 30 min to DCs, NIH3T3 and MEFs; 50 µM LY294002 (Calbiochem) was added to DCs 1 h before harvesting. Immature DCs were treated for the indicated time with 100 ng/ml LPS (SIGMA).

Affymetrix MicroArray Hybridization and Data Mining

Total RNA was extracted from bmDCs at different times after poly I:C stimulation using the RNeasy miniprep kit (Qiagen). For each condition 100 ng of total RNA were employed to synthesize double-stranded cDNA using two successive reverse-transcription reactions according to standard Affymetrix protocols (GeneChip Two-Cycle Target Labelling, Affymetrix). Linear amplification with T7-RNA polymerase and biotin labelling were performed by in vitro transcription by standard Affymetrix procedures. The resulting biotin-labeled cRNA was fragmented and hybridized to the Affymetrix Mouse Genome MOE 430 2.0 oligonucleotide 39,000-gene microarray chip for 16 h at 45° C. Following hybridization, the probe array was washed and stained on a fluidics station and immediately scanned on a Affymetrix GCS 3000 GeneArray Scanner. The data generated from the scan were then analyzed using the MicroArray Suite software (MAS 5.0, Affymetrix) and normalized using the GC-RMA algorithm. Bioinformatic analysis was performed using the GeneSpring GX 9.0 software (Agilent).

mRNA Quantification by Real-Time RT-PCR

Total RNA was isolated from DCs using the RNeasy miniprep kit (Qiagen). cDNA was synthesized from RNA samples using the Superscript II reverse transcriptase (Invitrogen). Quantitative real-time PCR was carried out in complete SYBR Green PCR buffer (PE Biosystem) by using 200 nM of each specific primer. A total of 20 µl of PCR mix was added to 5 µl of cDNA template, and the amplification was tracked via SYBR Green incorporation by using a Stratagene sequence detection system. cDNA concentration in each sample were normalized by using HPRT. A nontemplate control was also routinely performed. Primers used for gene amplification (designed with the Primer3 software) have been generated.

Translation Intensity Measurement

Puromycin labelling for measuring the intensity of translation was performed using 10 µg/ml puromycin (SIGMA, min 98% TLC, cell culture tested, P8833, diluted in PBS) was added in the culture medium and the cells were incubated for 10 min at 37° C. and 5% $CO_2$. Where indicated, 25 µM cycloheximide (SIGMA) was added 5 min before puromycin. Cells were then harvested, centrifugated at 4° C. and washed with cold PBS prior to cell lysis and immunoblotting with the 12D10 antibody.

Immunoblotting

Cells were lysed in 1% Triton X-100, 50 mM Hepes, 10 mM NaCl, 2.5 mM $MgCl_2$, 2 mM EDTA, 10% glycerol, 1 mM PMSF, supplemented with Complete Mini Protease Inhibitor Cocktail Tablets (Roche). Protein quantification was performed using the BCA Protein Assay (Pierce). 25-50 µg of Triton X-100-soluble material were loaded on 2%-12% gradient SDS-PAGE before immunoblotting and chemiluminescence detection (SuperSignal West Pico Chemiluminescent Substrate, Pierce). Nuclear extraction was performed using the Nuclear Complex Co-IP kit (Active Motif). Rabbit polyclonal antibodies against ATF4 (CREB-2, C-20) and eIF2α (FL-315) were from Santa Cruz Biotechnology, as well as mouse monoclonal against GADD34 (C-19) and PKR (B-10). Rabbit polyclonal antibodies against P-eIF2α (Ser 51) and caspase-3 were from BioSource and Cell Signaling Technology respectively. Mouse monoclonal antibodies against β-actin and histone H1 were from SIGMA and Upstate respectively. Secondary antibodies were from Jackson ImmunoResearch Laboratories. Quantification of eIF2α phosphorylation was performed using the Multi Gauge software (Fujifilm).

Immunocytochemistry

DCs were harvested and let adhere on 1% Alcian Blue-treated coverslips for 10 min at 37° C., fixed with 3% paraformaldeyde in PBS for 10 min at room temperature, permeabilized with 0.5% saponin in PBS/5% FCS/100 mM glycine for 15 min at room temperature and stained 1 h with indicated primary antibody. Goat polyclonal antibody against eIF4A (N-19) was from Santa Cruz; rat monoclonal antibody against Lamp2 was from I. Mellman's lab. All Alexa secondary antibodies (30 min staining) were from Molecular Probes (Invitrogen). Poly I:C was coupled with Cy5 using the LabeIT Cy5 labeling kit (Mirus). Immunofluorescence and confocal microscopy (using microscope model LSM 510; Carl Zeiss MicroImaging) were performed using a 63× objective and accompanying imaging software.

mRNA In Situ Hybridization

Stress granules formation was detected by in situ hybridization with oligo-dT (Alexa Fluor 555 dT18, Invitrogen). Cells were fixed with PFA, permeabilized with methanol 10 min at 20° C. and incubated with oligodT for 4 h at 43° C. Next, staining with the primary and secondary antibodies was performed.

IFN-β ELISA

IFN-β quantification in culture supernatant of DCs (5 fold-diluted) was performed using the Mouse Interferon Beta ELISA kit (PBL InterferonSource) according to manufacturer instructions.

Flow Cytometry Analysis

Cells were stained with specific antibodies for cell surface markers: CD86-biotin, IA/IE-PE and CD11c-APC (BD Pharmingen) (30 min at 4° C., in PBS/1% FCS). After washing, cells were stained with PerCP-Cy5.5 streptavidin (BD Pharmingen) (20 min at 4° C., in PBS/1% FCS), then washed and fixed in 2% paraformaldehyde in PBS. Events were collected on a FACScalibur (Becton Dickinson) and the data were acquired using the CellQuest software (BD Biosciences) and analysed using the FlowJo software.

Results

DC Stimulation by Poly I:C Induces Part of the ISR Genes

Protein synthesis is tightly regulated in activated mouse bone marrow-derived DCs [Lelouard, H. et al., 2007]. To identify potential molecules involved in this control, we performed genome-wide expression analysis of poly I:C stimulated DCs using Affymetrix Mouse Genome 430 2.0 arrays. We found that at least nine transcripts, typically expressed during the tunicamycin-induced Unfolded Protein Response (UPR) [Harding, H. P. et al., 2003; Okada, T., et Al., 2002; Marciniak, S. J. et al., 2004] were strongly induced. In particular, transcripts coding for the transcription factors ATF4, ATF3 and CHOP (Ddit3/GADD153) as well as for MyD116 (GADD34), tryptophanyl-tRNA synthetase (Wars), the COP2 component Sec23b and the disulfide-bond isomerase Ero11 and were all upregulated. The upregulation of these transcripts was confirmed by quantitative RT-PCR (qPCR), demonstrating the existence of an UPR-related gene expression signature in poly I:C stimulated DCs.

ATF4 and CHOP (Ddit3/GADD153) induction is one of the hallmarks of the UPR [Harding, H. P. et al., 2000]. ATF4 and CHOP mRNA expression was found by quantitative PCR (qPCR) to be respectively increased by 2 and 8 folds (FIGS. 1a and 1b) in response to poly I:C. ATF4 mRNA is normally expressed in unstressed cells but is poorly translated. However, upon stress-mediated eIF2-α phosphorylation, a rapid synthesis of the ATF4 protein can be observed [Harding, H. P. et al., 2000; Scheuner, D. et al., 2001; Lu, P. D., et Al., 2004]. ATF4 synthesis induces CHOP/GADD153 expression, which in turn triggers the transcription of many downstream target genes important for the response to a variety of stress that result in growth arrest or DNA damage (GADD) [Marciniak, S. J. et al., 2004]. Therefore, we monitored ATF4 levels by immunoblot during DC activation. ATF4 translation was strongly up-regulated upon poly I:C stimulation and the protein was mostly detected in the nucleus after 8 h of stimulation. Interestingly, induction levels were similar to those induced by tunicamycin (FIG. 1a). Thus, ATF4 expression is induced by poly I:C detection and drives the transcription of CHOP and its downstream effectors.

GADD34 Upregulation in Activated DCs

Figure 1C:
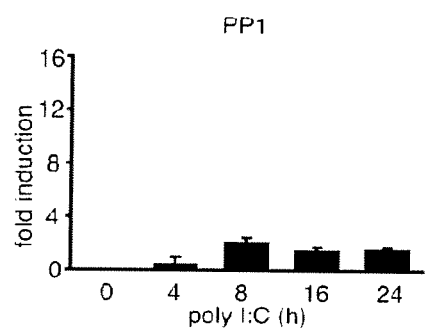
Figure 1E:
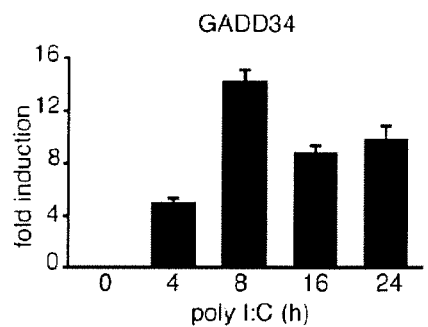
Figure 1E:
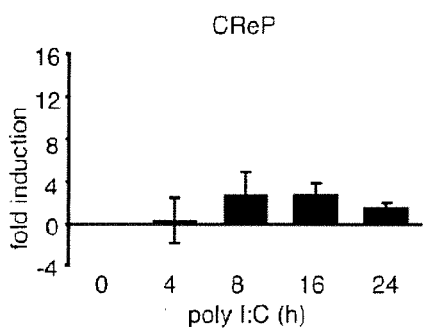
Figure 1D:
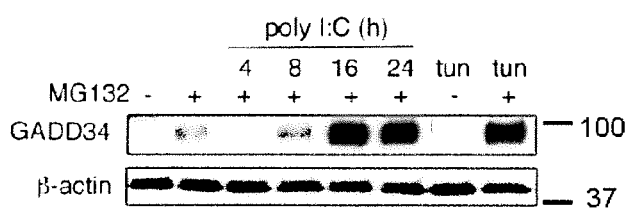

One of the main downstream targets of CHOP is GADD34 (MyD116), which serves to relieve translation repression during ER stress [Marciniak, S. J. et al., 2004; Novoa, I., et Al., 2001; Novoa, I. et al., 2003]. GADD34 inhibits the catalytic subunit of protein phosphatase 1 (PP1) that dephosphorylates eIF2-α. The expression of PP1 and GADD34 in activated DCs was monitored by qPCR (FIGS. 1c and 1d). PP1 mRNA expression was modestly increased upon poly I:C exposure. In contrast, GADD34 mRNA transcription was enhanced at least 14 folds during maturation. GADD34 contains two PEST sequences promoting rapid proteasome-mediated degradation. Thus, proteasome inhibition by MG132 was necessary to allow GADD34 detection in cell extracts (FIG. 1d). As expected from the transcriptional analysis, the protein was found to accumulate progressively during DC activation, peaking after 8 h of stimulation and in comparable amounts to the levels induced by tunicamycin (FIG. 1d). Thus poly I:C stimulation induces in DCs the transcription and synthesis of several important components of the UPR including ATF4, CHOP and GADD34. Importantly, GADD34, being a potent cofactor of PP1, is considered as part of the negative feedback loop reducing translational stress during the UPR [Novoa, I., et Al., 2001; Novoa, I. et al., 2003]. In contrast, the constitutive PP1 cofactor CReP (constitutive repressor of eIF2-α phosphorylation [Jousse, C. et al., 2003]) was induced only very modestly upon DC maturation (FIG. 1e), suggesting no major role of this molecule during poly I:C detection.

eIF2-α is Dephosphorylated During DC Activation

Protein synthesis in DCs was quantified using puromycin labelling followed by immunoblot with the anti-puromycin mAb 12D10 (FIG. 2a). As previously demonstrated for LPS-activated DCs, protein synthesis is enhanced in the first hours of poly I:C stimulation followed by a reduction after 12-16 h of activation [Lelouard, H. et al., 2007]. Immunoblot and quantification for phosphorylated (P-eIF2-α) and total eIF2-α were also performed on the same DC extracts (FIG. 2b). Interestingly P-eIF2-α levels were found to be gradually reduced during poly I:C stimulation.

The loss of P-eIF2-α in poly I:C treated cells, which at this late time of maturation display a reduced protein synthesis rate, indicates that eIF2-α phosphorylation is probably not involved in translation inhibition. However, since eIF2-α phosphorylation intensity was inversely correlated with GADD34 expression levels, we tested how targeted inhibition of the PP1-GADD34 complex activity with the specific inhibitor salubrinal [Boyce, M. et al., 2005] could affect eIF2-α in DCs. Salubrinal alone induced eIF2-α phosphorylation (FIG. 2c), which was considerably enhanced in presence of soluble poly I:C. These results were confirmed using tautomycin, another PP1 inhibitor. Thus, eIF2-α kinases are functional in DCs and PP1 activity is responsible for the dephosphorylation of eIF2-α through the enhanced GADD34 expression triggered by poly I:C detection.

PKR is Functional and Phosphorylates eIF2-α in Activated DCs.

PKR functions as a signal transducer in the proinflammatory response to different microbial products, including LPS and dsRNA. Alternatively, activation of PKR during infection by viral dsRNA results in eIF2-α phosphorylation and inhibition of protein synthesis. To gain further insights on the role of PKR during DC activation, wild-type and PKR$^{-/-}$ cells were monitored for eIF2-α phosphorylation upon poly I:C stimulation (FIG. 3a). Immature DCs displayed relatively low levels of PKR, which were strongly upregulated upon maturation. Interestingly, PKR levels were inversely correlated with the intensity of eIF2-α phosphorylation, which was gradually reduced during maturation. In non-activated PKR$^{-/-}$ DCs, levels of P-eIF2-α were close to normal, confirming that other kinases than PKR phosphorylate eIF2-α in immature DCs (FIG. 3a). However upon poly I:C exposure, eIF2-α phosphorylation was nearly abolished in these cells, confirming that PKR normally mediates eIF2-α c phosphorylation upon poly I:C detection, but its activity is counteracted by PP1 activation. This mechanism was also able to limit eIF2-α phosphorylation upon direct delivery of poly I:C in the DC cytosol (FIG. 3b), a mode of targeting which induces PKR-dependent eIF2-α phosphorylation in wild-type MEFs and NIH3T3 cells (FIG. 3c). Although the deletion of PKR impacted the total levels of P-eIF2-α in MEFs, poly I:C stimulation did not influence its phosphorylation compared to control cells, indicating that the dephosphorylation induced by dsRNA detection in DCs does not occur in fibroblasts. In agreement with this observation, GADD34 levels in NIH3T3 cells were found unchanged if not decreased in response to poly I:C lipofection (FIG. 3d).

Protein Synthesis is not Inhibited in DCs Exposed to Cytosolic Poly I:C

Translation was monitored in DCs and fibroblasts exposed to soluble or lipofected poly I:C for several hours. Lipofection of poly I:C in MEFs (wt and PKR$^{-/-}$) and NIH3T3 efficiently induced PKR-dependent translation arrest within 4 to 8 hours (FIG. 4a). Interestingly, although soluble poly I:C did not affect NIH3T3 cells, translation was inhibited in wt MEFs, suggesting that soluble dsRNA can access efficiently to the cytosol of these cells and interact with PKR. In the case of DCs, and as anticipated from the low levels of eIF2-α phosphorylation induced by poly I:C lipofection, translation was not inhibited even after 8 hours of exposure (FIG. 4a). Interestingly, while we verified by FACS that equivalent amounts of poly I:C were delivered in the cells by lipofection (FIG. 4b), we visualized poly I:C entry. In addition of detecting the accumulation of lipofected poly I:C in large cytosolic aggregates, we could also show that soluble poly I:C penetrates in the DC cytoplasm and appears as speckles situated away from LAMP2-positive endo/lysosomes, a phenomenon never observed in NIH3T3 cells.

This relatively efficient access of soluble poly I:C to DC cytosol suggests that PKR could be activated concomitantly with TLR3 and MDA5. This hypothesis is supported by the observation that soluble poly I:C strongly accentuates eIF2-α phosphorylation in presence of salubrinal, which inhibits specifically the PP1/GADD34 activity (FIG. 2c). Moreover, protein synthesis in poly I:C stimulated DCs was strongly reduced in presence of salubrinal (FIG. 4c), suggesting that activated DCs rely on the induction of PP1/GADD34 activity to resist PKR-dependent translational arrest by shifting the biochemical equilibrium toward eIF2-α dephosphorylation.

Signal Transduction Pathways Involved in GADD34 Transcription Upregulation

We used DCs generated from mice lacking the dsRNA sensors TLR3 and MDA5 to determine the signaling cascade responsible for the triggering of eIF2-α dephosphorylation (FIG. 5). DCs were stimulated with poly I:C as indicated prior immunoblotting for P-eIF2-α (FIG. 5a). Single inactivation of TLR3 or MDA5 did not affect eIF2-α phosphorylation compared to control cells. Thus, the cascade inducing GADD34 expression can be probably triggered by the stimulation of any of these receptors, which is likely to occur in the endosomes or via the passage of poly I:C in the cytosol. Recently, we have shown that PI3 kinase activation is necessary to achieve full DC maturation in response to TLR ligation and that is involved in controlling translation upregulation [Lelouard, H. et al., 2007]. We therefore monitored eIF2-α phosphorylation in presence of the PI3K inhibitor LY294002 (LY) (FIG. 5a). LY treatment efficiently prevented eIF2-α dephosphorylation, indicating that PI3K signaling and the induction of the stress response pathway in activated DCs are tightly linked. The relatively late stage of maturation at which eIF2-α is dephosphorylated led us to investigate whether the autocrine activity of IFN-β could be involved in this process. Although IFN receptor signaling is required to achieve normal DC maturation and abundant IFN-β production (FIG. S3), no change in eIF2-α phosphorylation was observed in poly I:C-activated IFN-αβ receptor$^{-/-}$ (IFN-αβ R$^{-/-}$) DCs (FIG. 5b). In contrast, qPCR quantification indicated that GADD34 mRNA levels were reduced by two to six folds compared to wt cells (FIG. 5c).

Interestingly, IFN-β receptor signalling was also shown to be responsible for the strong upregulation of PKR during DC maturation (FIG. 5b). This lack of PKR upregulation could therefore compensate for the relative loss of GADD34 activity in stimulated IFN-αβ R$^{-/-}$ DCs, explaining why the rate of eIF2-α dephosphorylation remains unchanged or is even higher at late time points. Thus, the autocrine effect of IFN-β on DCs contributes significantly to GADD34 induction.

Activated DCs Resist to Stress Inducing Translation Inhibition

As seen with poly I:C, eIF2-α dephosphorylation is likely to increase DC resistance to other stress causing translational arrest. Arsenite treatment induces the formation of stress granules (SG), which serves as depository of mRNA and translational factors and require eIF2-α phosphorylation for their formation [Kedersha, N. & Anderson, P., 2002; Anderson, P. & Kedersha, N, 2002; Kedersha, N. et al., 2005]. SG induction by arsenite was visualised by confocal microscopy detection of poly-A mRNA and eIF4a during DC stimulation by poly I:C or LPS (FIG. 6a). SGs were found in almost 100% of non-activated DCs, a proportion which was progressively reduced to 15% upon activation. Interestingly, the intensity and kinetics of SG formation mirrored perfectly the state of eIF2-α phosphorylation and GADD34 expression induced by poly I:C or LPS (FIG. 6a). Surprisingly, the kinetics of eIF2-α dephosphorylation in LPS stimulated DCs were strikingly different from those induced by poly I:C.

Amino acids starvation is also known to induce eIF2-α phosphorylation. Interestingly, tryptophan depletion mediated by the enzyme indoleamine 2,3-dioxygenase (IDO), which is produced in activated DCs, promotes peripheral tolerance by causing T cell anergy [Mellor, A. L. & Munn, D. H., 2004; Puccetti, P., 2007]. The GCN2 kinase in T cells is partially responsible for this phenomenon by sensing deacylated tryptophan-tRNAs and causing eIF2-α phosphorylation [Munn, D. H. et al., 2005]. We tested whether DC activation would also prevent translation arrest upon tryptophan starvation. Translation inhibition and eIF2-α phosphorylation in response to tryptophan depletion were clearly observed in wt MEFs grown in tryptophan-free media for 6 hours but not in GCN2$^{-/-}$ MEFs (FIG. 6b). In MEFs, translation inhibition was already detectable after 2 h of starvation and total after 8 h, concomitantly with an enhancement in eIF2-α phosphorylation. Based on these observations, DCs were activated during 2 h with poly I:C prior tryptophan starvation (keeping poly I:C during starvation). Contrary to MEFs, activated DCs, submitted to tryptophan depletion, did not exhibit any translation inhibition over 6 hours, presumably due to induction of GADD34 and its subsequent control of eIF2-α phosphorylation (FIG. 6b). The inducible expression in DCs of tryptophanyl-tRNA synthetase (Wars) at these times could also favor protein synthesis in tryptophan starvation conditions and accentuate the phenotype. Unfortunately, we could not monitor translation activity in non-stimulated DCs, since the experimental starvation conditions, used here, induced their spontaneous maturation and/or cell death. Thus, activated DCs specifically display an acute resistance to most of the stress inducing eIF2-α phosphorylation and inhibiting cap-mediated translation.

eIF2-α Phosphorylation and DC Function

PKR has been shown to be an important mediator of cytokine production and apoptosis through eIF2-α phosphorylation and p38 pathway activation, notably upon LPS detection by macrophages [Hsu, L. C. et al., 2004]. We therefore evaluated the impact of eIF2-α phosphorylation on IFN-β expression, the major cytokine produced by DCs upon poly I:C stimulation [Diebold, S. S. et al., 2007] (FIG. 7a). PKR$^{-/-}$ DCs stimulated with poly I:C displayed extremely reduced levels of IFN-β secretion compared to wt cells, thus confirming the requirement of PKR activation for this process [Samuel, C. E., 2001]. We next tested the impact of GADD34/PP1 inhibition on IFN-β secretion by DCs. Upon salubrinal treatment, IFN-β secretion was drastically reduced in poly I:C treated DCs, indicating that uncontrolled eIF2-α phosphorylation during PKR activation could impair normal IFN-β production. Thus GADD34 expression is required to compensate for concomitant PKR activation and achieve functional maturation during DC activation.

We further tested if deregulated eIF2-α phosphorylation could also lead to apoptosis in activated DCs [Scheuner, D. et al., 2006; Rintahaka, J., et Al., 2008]. DCs were exposed to various stimuli and pharmacological treatments prior caspase-3 detection by immunoblotting (FIG. 7b). Although addition of poly I:C or LPS had little effect, salubrinal treatment alone induced a massive increase in total levels of caspase-3 and in its cleaved active product, generally seen as an important step for apoptosis initiation. Thus, eIF2-α phosphorylation seems to have a direct effect on the synthesis and the cleavage of caspase-3. Treatments with both salubrinal and poly I:C or LPS had a lighter effect than salubrinal alone, probably due to GADD34 induction in activated DCs which renders them more resistant to salubrinal induced inhibition. These experiments confirm the need of controlling eIF2-α phosphorylation to avoid abnormal induction of caspase-3, a situation, which would normally be prevented by GADD34 expression and eIF2-α dephosphorylation in activated DCs.

Figure 10:
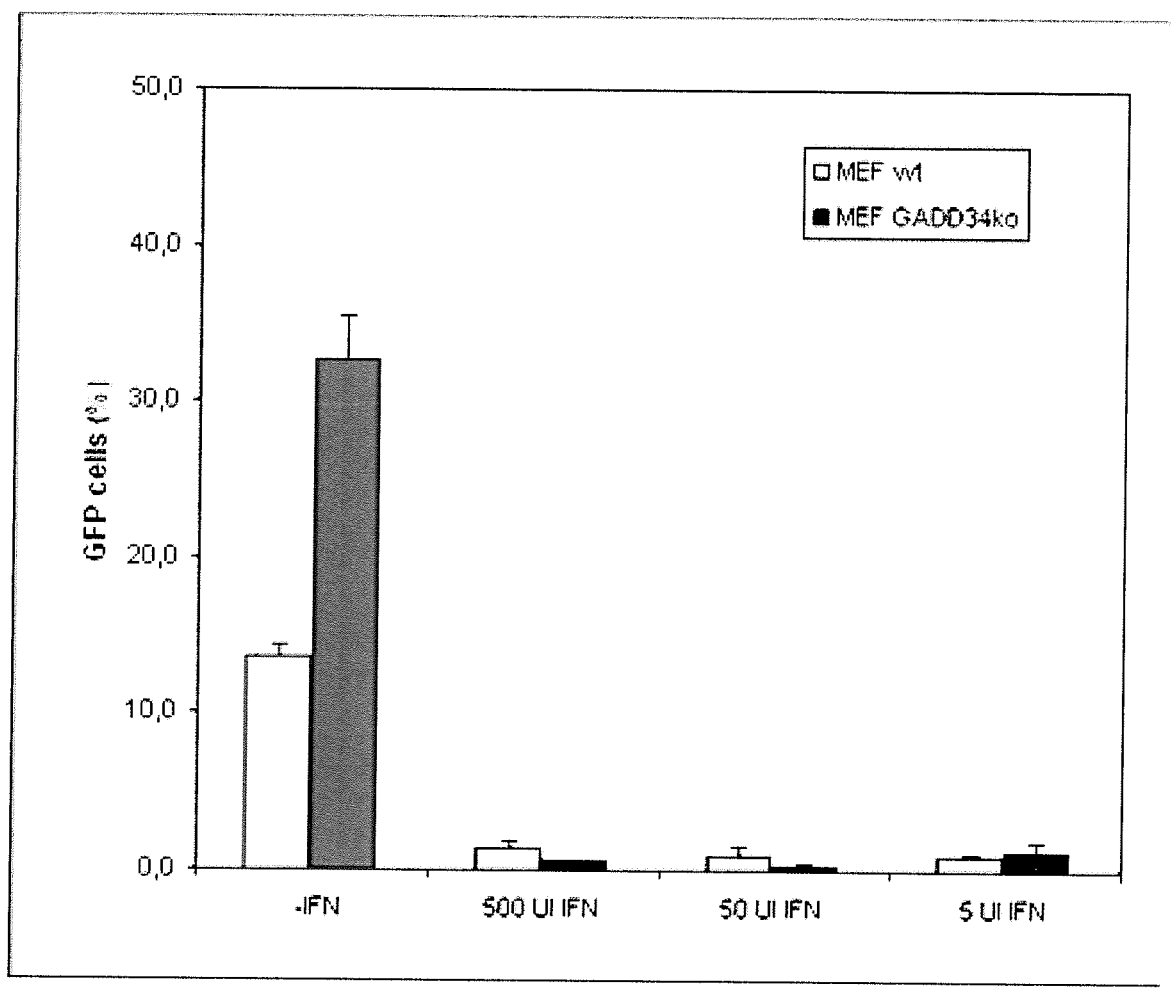

GADD34 Expression is Necessary to Produce Cytokines in Fibroblasts in Response to dsRNA Cytosolic poly I:C detection in mouse embryonic fibroblasts (MEFs) also promotes a PKR-dependent mRNA translation arrest and an ISR-like response, during which, ATF4 and its downstream target the phosphatase-1 (PP1) cofactor, growth arrest and DNA damage-inducible protein 34 (GADD34/MyD116/Ppp1r15a) are strongly up-regulated. Interestingly, although most of mRNA translation is strongly inhibited by poly I:C, IFN-beta (IFN-β), Interleukin-6 (IL-6) and PKR synthesis are all considerably increased in these conditions. We further demonstrate that PKR-dependent expression of GADD34 is absolutely required for the normal translation of IFN-β and IL-6 mRNAs, while dispensable for PKR neo-synthesis (FIG. 9). We have recapitulated these observations using CHIKV as a pathological-relevant model and show that GADD34-deficient MEFs are extremely permissive to the virus due to their inability to produce type-I interféron (FIG. 10). We further show that, although normal 12 days old mice are fully resistant to CHIKV infection, GADD34-deficiency induces 100% of mortality among the neonates of the same age (FIG. 11). Our observations demonstrate that induction of the ATF4 transcription program is part of the anti-viral response and imply the existence of several distinct and segregated group of mRNA translated differently during dsRNA-induced eIF2-α phosphorylation.

DISCUSSION

Translation inhibition occurs in response to many stress in which cellular activity has to be orientated or suspended momentarily. We demonstrate here that the cellular defense pathways involving the different PKR-like kinases and eIF2-α phosphorylation are inactivated in activated DCs. We have shown that poly I:C treated cells display a gene expression signature sharing common features with an integrated stress response, including CHOP and GADD34 induction. Interestingly GADD34 induction was also recently singled out in a transcriptome analysis of *Lysteria monocytogenes*-infected macrophages [Leber, J. H. et al., 2008], suggesting that its expression is associated with pathogen detection in different APCs. GADD34 associates with the catalytic subunit of PP1, which dephosphorylates eIF2-α and counteracts PKR-like kinases activity.

During our investigations, we could not identify a unique signaling pathway responsible for GADD34 induction. GADD34 expression has been primarily shown to operate as a negative feedback loop during unfolded protein responses (UPR). DCs have also been reported to express unusually high levels of XBP-1, a transcription factor essential for ER homeostasis during UPR [Ron, D. & Walter, P., 2007; Yoshida, H., et Al., 2001; Calfon, M. et al., 2002], which is necessary for normal DC survival and function including IFN-β expression [Iwakoshi, N. N., et Al., 2007; Smith, J. A. et al., 2008]. Moreover, we have shown that DC activation leads to a massive increase in protein translation as well as the production of numerous cytokines, which are mostly using the ER-mediated secretion pathway. Interestingly, LPS and poly I:C induce differently GADD34, while also triggering different levels and kinetics of cytokines production. Moreover, GADD34 expression is decreased in activated IFN-αβ R$^{-/-}$ DCs, which produce reduced levels of cytokines in response to microbial products. Finally, eIF2-α dephosphorylation is prevented by the PI3K pharmacological inhibitor LY294002, which has also a strong inhibitory effect on protein synthesis [Lelouard, H. et al., 2007]. GADD34 expression is therefore tightly linked to the intensity of protein synthesis and cytokine production in activated DCs. It is possible that the burst of protein synthesis early during DC maturation could promote a transient UPR-like situation leading to ATF4 translation and subsequent GADD34 expression. Interestingly, although eIF2-α is clearly phosphorylated in immature DCs, no major increase in this phosphorylation was observed during the first phase of activation to fully explain ATF4 translation. Thus, the transcriptional response to poly I:C detection is relatively different from what is normally observed during previously characterized UPRs and potentially involves a novel signaling mechanism capable of inducing ATF4 production.

We have shown that soluble dsRNA access rapidly the cytosol of DCs and has therefore the potential to interact with both MDA5 and PKR. PKR is rapidly activated by TLR ligands to promote p38 and NF-κB signaling [Williams, B. R., 2001]. PKR activation is therefore necessary to achieve functional DC maturation, however its activation should also normally lead to translation inhibition through eIF2-α phosphorylation. The existence of the ATF4/GADD34 response could therefore be adapted to the microbial stimuli detected and the levels of PKR activation required to achieve functional DC maturation. Poly I:C is probably an extreme example since it can induce PKR through TLR signaling and also through direct recognition. This negative control loop would be particularly important to avoid premature apoptosis and to ensure optimal cytokine production.

GADD34 induction could also have some additional protective effect against some aspects of DC maturation itself. Indeed, indoleamine 2,3-dioxygenase (IDO) and heme-oxygenase-I (HO-1) are two catabolic enzymes produced by tumors and mature DCs, which shape the immune response by depleting respectively tryptophan and porphyrin in the DC vicinity [Munn, D. H. et al., 2005; Uyttenhove, C. et al., 2003; Chauveau, C. et al., 2005; Munn, D. H., 2006]. Neighboring T cells exposed to these conditions are anergized or differentiated through the activation of GCN2 (tryptophan depletion) or HRI (heme depletion). GADD34 expression could therefore protect DCs from the detrimental effects of tryptophan starvation and also probably of heme depletion triggered by their own activation or the activation of neighboring DCs. This specificity allows DCs to prioritize the signaling transduction pathways governing their innate immunity function over the pathways normally protecting their cellular integrity from stress which, if activated, would lead to translational arrest, apoptosis or anergy in most cells types [Freigang, S., et Al., 2005].

EXAMPLE 2: GADD34 IS NECESSARY TO CONTROL CHIKUNGUNYA VIRUS INFECTION AND IFN PRODUCTION IN VITRO AND IN VIVO

Material & Methods
Virus.

CHIKV isolates were obtained from individuals during the 2005-06 CHIKV outbreak in La Reunion Island and amplified on mosquito C6/36 cell as described [4]. CHIKV-21 was isolated from the serum of a newborn male with CHIKV-associated encephalopathy; CHIKV-27 was isolated from the CSF of another new-born male with encephalopathy; CHIKV-115 from the serum of a 24-year old female with classical CHIK symptoms. CHIKV-117 was isolated at the Institut de Médecine Tropicale du Service de Santé des Armees (IMTSSA), Marseille, France during the 2000 CHIKV outbreak in Democratic Republic of the Congo from the serum of a person presenting classical CHIK symptoms. Titers of virus stocks were determined by standard Vero cell plaque assay and are expressed as PFU per ml.

Cells.

Control and GADD34–/– mouse embryonic fibroblasts were infected with CHIKV at a multiplicity of infection (MOI) of 10 and 50.

Animals.

Inbred FVB mice were obtained from Charles River laboratories (France). Mice were bred according to the Institut Pasteur guidelines for animal husbandries and were kept in level-3 isolators. Mice were inoculated by ID in the ventral thorax with 50 μl of a viral suspension diluted with PBS for adult mice and with 30 μl for neonates. Mock-infected mice received PBS alone. Mice were anesthetized with isoflurane (Forene, Abbott Laboratories Ltd, United-Kingdom). Blood was collected by cardiac puncture after which each mouse was perfused via the intracardiac route with 40 ml of PBS at 4° C. before harvesting of organs. Tissues were homogenized, and virus titers of each tissue sample determined on Vero cells by tissue cytopathic infectious dose 50 (TCID50), and viral titers in tissues and in serum were expressed as TCID50/g or TCID50/ml, respectively. The principles of good laboratory animal care were followed all through the experimental process. Mortality studies were performed on groups of six mice and viral titers in tissues from four mice at each time point.

Histology and Immunofluorescence.

Mouse organs were snap frozen in isopentane cooled by liquid nitrogen for cryosectionning or fixed in para-formaldehyde for paraffin embedding. Paraffin-embedded tissues were processed for histological staining (Hematoxylin and eosin). For immunofluorescence, cryosections were fixed for 10 min in ice-cold methanol before incubation for 12 h at 4°

C. with the primary antibodies followed by incubation for 1 h with the secondary antibodies. Slides were counterstaining with Hoechst (Vector Lab). The following antibodies were used: polyclonal rabbit anti-collagen IV (Chemicon, Temecula Calif., 1:200), polyclonal chicken anti-vimentin (Abcam, Cambridge, UK, 1:200), monoclonal mouse anti-GFAP (BD pharmingen 1:1,000 or 1:5,000 to only see the glia limitans), monoclonal rat anti-macrophage antigen F4/80 (Abcam, 1:100), polyclonal rabbit anti-PECAMI/CD31 (Abcam, 1:400), human serum anti-CHIKV were obtained and characterized by the Centre National de Référence des Arbovirus as positive for anti-CHIKV IgM and IgG. The marker specificities were systematically confirmed by examining sections in which the primary antibody was replaced by control isotype or immunoglobulins at the same concentration and by immunostaining of non-infected tissues from the same animal strain. Slides were examined with a Zeiss AxioPlan 2 microscope equipped with an ApoTome system in order to obtain 0.7 µm thick optical sections. Pictures and Z-stacks were obtained using the AxioVision 4.5 software. When necessary, images were processed using the image J software (http://rsb.info.nih.gov.gate2.inist.fr/ij/).

Results

Fibroblast of both human and mouse origin constitutes a major target cell of CHIKV at the acute phase of the infection. In adult mouse with a totally abrogated type-I IFN signaling, CHIKV-associated disease is particularly severe and correlates with higher viral loads. Importantly, mice with one copy of the IFN-α/β receptor (IFNAR) gene develop a mild disease, strengthening the implication of type-I IFN signaling in the control of CHIKV replication. CHIKV is therefore a particularly relevant pathogen to confirm our observations on the role of PKR and GADD34 in controlling type-I IFN production in response to dsRNA. Mouse wt and GADD34ΔC/ΔC MEFs were exposed to 106 PFU CHIKV (range 0.1-50 multiplicity of infection [MOI]) for 24 or 48 h. Culture supernatants were monitored for the presence of type I IFNs, while productive infection was estimated by GFP expression (FIGS. 10A and B). Productive CHIKV infection could only be observed at maximum MOI in wt MEFs, while IFN-β was detected at low MOI and robust amount were produced at a higher range of infection. Contrasting with these results, a very high level of viral replication was observed in GADD34ΔC/ΔC MEFs, which were exquisitely sensitive to CHIKV displaying a 50% infection rate compared to the mere 15% observed in wt MEFS after 24 h of infection (MOI 50). Correlated with this hypersensitivity, IFN-β production could not be detected during CHIKV infection of GADD34ΔC/ΔC MEFs, indicating again their incapacity to produce cytokines in response to cytosolic dsRNA, which is likely to facilitate viral replication in the culture. This interpretation is clearly supported by the similar abrogation of viral replication in both WT and GADD34ΔC/ΔC MEFs briefly treated with IFN-β prior infection (FIG. 10C), demonstrating that GADD34 inactivation does not favor viral replication in presence of sufficient IFN levels.

Like in Humans, CHIKV pathogenicity is strongly age-dependent in mice, and in less than 12 day-old mouse neonates, CHIKV induces a severe disease accompanied with a high rate of mortality [Couderc, 2008]. Several components of the innate immune response have been shown to impact on the resistance of older mice to restrict efficiently CHIKV infection and its consequences. Intra-dermal (ID) injections of 106 PFU of CHIKV were performed in wt (FVB) and GADD34ΔC/ΔC neonates mice to determine the importance of the GADD34 pathway during the establishment of the innate anti-viral response in whole animals. As previously observed for C57/BL6 mice [Couderc, 2008], when CHIKV inoculation was performed on 12 days old FVB neonates, a 100% survival rate was observed among the pups (FIG. 11). Strongly contrasting with these results, 12 days old GADD34ΔC/ΔC neonates all died within 72 h of CHIKV infection (FIG. 11). Further demonstrating that functional GADD34 expression is a key component of the anti-viral pathway and is forming with ATF4 and PKR a signaling module specialized in the type-I IFN response to specific viruses including the alphavirus group and probably several other viral families which are detected by MDA5 and PKR.

These results show that inhibiting the formation of the PP1/GADD34 complex by using an inhibitor as defined above may be useful for decreasing the capacity of cells to produce cytokines. Inhibitors according to the invention may thus be used to treat inflammatory conditions such as sepsis or exacerbated inflammatory conditions caused by an infectious or viral disease.

REFERENCES

Throughout this application, various references describe the state of the art to which this invention pertains. The disclosures of these references are hereby incorporated by reference into the present disclosure.

Alexopoulou, L., Holt, A. C., Medzhitov, R. & Flavell, R. A. Recognition of double-stranded RNA and activation of NF-kappaB by Toll-like receptor 3. Nature 413, 732-8 (2001).

Anderson, P. & Kedersha, N. Stressful initiations. J Cell Sci 115, 3227-34 (2002).

Berlanga, J. J. et al. Antiviral effect of the mammalian translation initiation factor 2alpha kinase GCN2 against RNA viruses. Embo J 25, 1730-40 (2006).

Boyce, M. et al. A selective inhibitor of eIF2alpha dephosphorylation protects cells from ER stress. Science 307, 935-9 (2005).

Calfon, M. et al. IRE1 couples endoplasmic reticulum load to secretory capacity by processing the XBP-1 mRNA. Nature 415, 92-6 (2002).

Chauveau, C. et al. Heme oxygenase-1 expression inhibits dendritic cell maturation and proinflammatory function but conserves IL-10 expression. Blood 106, 1694-702 (2005).

Chen, J. J. & London, I. M. Regulation of protein synthesis by heme-regulated eIF-2 alpha kinase. Trends Biochem Sci 20, 105-8 (1995).

Connor, J. H., Weiser, D. C., Li, S., Hallenbeck, J. M. & Shenolikar, S. Growth arrest and DNA damage-inducible protein GADD34 assembles a novel signaling complex containing protein phosphatase 1 and inhibitor 1. Mol Cell Biol 21, 6841-50 (2001).

Couderc T, Chrétien F, Schilte C, Disson O, Brigitte M, Guivel-Benhassine F, Touret Y, Barau G, Cayet N, Schuffenecker I, Despres P, Arenzana-Seisdedos F, Michault A, Albert M L, Lecuit M. A mouse model for Chikungunya: young age and inefficient type-I interferon signaling are risk factors for severe disease. PLoS Pathog. 2008 Feb. 8; 4(2):e29.

Diebold, S. S. et al. Viral infection switches non-plasmacytoid dendritic cells into high interferon producers. Nature 424, 324-8 (2003).

Donze, O. et al. The protein kinase PKR: a molecular clock that sequentially activates survival and death programs. Embo J 23, 564-71 (2004).

Freigang, S., Probst, H. C. & van den Broek, M. DC infection promotes antiviral CTL priming: the 'Winkelried' strategy. Trends Immunol 26, 13-8 (2005). Munn, D. H. Indoleamine 2,3-dioxygenase, tumor-induced tolerance and counter-regulation. Curr Opin Immunol 18, 220-5 (2006).

Gitlin, L. et al. Essential role of mda-5 in type I IFN responses to polyriboinosinic:polyribocytidylic acid and encephalomyocarditis picornavirus. Proc Natl Acad Sci USA 103, 8459-64 (2006).

Harding, H. P., Zhang, Y., Bertolotti, A., Zeng. H. & Ron, D. Perk is essential for translational regulation and cell survival during the unfolded protein response. Mol Cell 5, 897-904 (2000).

Harding, H. P. et al. Regulated translation initiation controls stress-induced gene expression in mammalian cells. Mol Cell 6, 1099-108 (2000).

Harding, H. P. et al. An integrated stress response regulates amino acid metabolism and resistance to oxidative stress. Mol Cell 11, 619-33 (2003).

Hsu, L. C. et al. The protein kinase PKR is required for macrophage apoptosis after activation of Toll-like receptor 4. Nature 428, 341-5 (2004).

Iwakoshi, N. N., Pypaert, M. & Glimcher, L. H. The transcription factor XBP-1 is essential for the development and survival of dendritic cells. J Exp Med 204, 2267-75 (2007).

Jousse, C. et al. Inhibition of a constitutive translation initiation factor 2alpha phosphatase, CReP, promotes survival of stressed cells. J Cell Biol 163, 767-75 (2003).

Kawai, T. & Akira, S. Innate immune recognition of viral infection. Nat Immunol 7, 131-7 (2006).

Kedersha, N. & Anderson, P. Stress granules: sites of mRNA triage that regulate mRNA stability and translatability. Biochem Soc Trans 30, 963-9 (2002).

Kedersha, N. et al. Stress granules and processing bodies are dynamically linked sites of mRNP remodeling. J Cell Biol 169, 871-84 (2005).

Leber, J. H. et al. Distinct TLR- and NLR-mediated transcriptional responses to an intracellular pathogen. PLoS Pathog 4, e6 (2008).

Lelouard, H. et al. Regulation of translation is required for dendritic cell function and survival during activation. J Cell Biol 179, 1427-39 (2007).

Lu, L., Han, A. P. & Chen, J. J. Translation initiation control by heme-regulated eukaryotic initiation factor 2alpha kinase in erythroid cells under cytoplasmic stresses. Mol Cell Biol 21, 7971-80 (2001).

Lu, P. D., Harding, H. P. & Ron, D. Translation reinitiation at alternative open reading frames regulates gene expression in an integrated stress response. J Cell Biol 167, 27-33 (2004).

Marciniak, S. J. et al. CHOP induces death by promoting protein synthesis and oxidation in the stressed endoplasmic reticulum. Genes Dev 18, 3066-77 (2004).

Mellman, I. & Steinman, R. M. Dendritic cells: specialized and regulated antigen processing machines. Cell 106, 255-8 (2001).

Mellor, A. L. & Munn, D. H. IDO expression by dendritic cells: tolerance and tryptophan catabolism. Nat Rev Immunol 4, 762-74 (2004).

Munn, D. H. et al. GCN2 kinase in T cells mediates proliferative arrest and anergy induction in response to indoleamine 2,3-dioxygenase. Immunity 22, 633-42 (2005).

Novoa, I., Zeng, H., Harding, H. P. & Ron, D. Feedback inhibition of the unfolded protein response by GADD34-mediated dephosphorylation of eIF2alpha. J Cell Biol 153, 1011-22 (2001).

Novoa, 1. et al. Stress-induced gene expression requires programmed recovery from translational repression. Embo J 22, 1180-7 (2003).

Okada, T., Yoshida, H., Akazawa, R., Negishi, M. & Mori, K. Distinct roles of activating transcription factor 6 (ATF6) and double-stranded RNA-activated protein kinase-like endoplasmic reticulum kinase (PERK) in transcription during the mammalian unfolded protein response. Biochem J 366, 585-94 (2002).

Proud, C. G. PKR: a new name and new roles. Trends Biochem Sci 20, 241-6 (1995).

Puccetti, P. On watching the watchers: IDO and type I/II IFN. Eur J Immunol 37, 876-9 (2007).

Rintahaka, J., Wiik, D., Kovanen, P. E., Alenius, H. & Matikainen, S. Cytosolic antiviral RNA recognition pathway activates caspases 1 and 3. J Immunol 180, 1749-57 (2008).

Ron, D. & Walter, P. Signal integration in the endoplasmic reticulum unfolded protein response. Nat Rev Mol Cell Biol 8, 519-29 (2007).

Samuel, C. E. Antiviral actions of interferons. Clin Microbiol Rev 14, 778-809, table of contents (2001).

Scheuner, D. et al. Translational control is required for the unfolded protein response and in vivo glucose homeostasis. Mol Cell 7, 1165-76 (2001).

Scheuner, D. et al. Double-stranded RNA-dependent protein kinase phosphorylation of the alpha-subunit of eukaryotic translation initiation factor 2 mediates apoptosis. J Biol Chem 281, 21458-68 (2006).

Smith, J. A. et al. Endoplasmic reticulum stress and the unfolded protein response are linked to synergistic IFN-beta induction via X-box binding protein 1. Eur J Immunol 38, 1194-203 (2008).

Todd, D. J., Lee, A. H. & Glimcher, L. H. The endoplasmic reticulum stress response in immunity and autoimmunity. Nat Rev Immunol 8, 663-674 (2008).

Uyttenhove, C. et al. Evidence for a tumoral immune resistance mechanism based on tryptophan degradation by indoleamine 2,3-dioxygenase. Nat Med 9, 1269-74 (2003).

Williams, B. R. PKR; a sentinel kinase for cellular stress. Oncogene 18, 6112-20 (1999).

Williams, B. R. Signal integration via PKR. Sci STKE 2001, RE2 (2001).

Yoshida, H., Matsui, T., Yamamoto, A., Okada, T. & Mori, K. XBPI mRNA is induced by ATF6 and spliced by IRE1 in response to ER stress to produce a highly active transcription factor. Cell 107, 881-91 (2001).

Zhang, P. et al. The GCN2 eIF2alpha kinase is required for adaptation to amino acid deprivation in mice. Mol Cell Biol 22, 6681-8 (2002).

Zhang, K. & Kaufman, R. J. From endoplasmic-reticulum stress to the inflammatory response. Nature 454, 455-62 (2008).

The invention claimed is:

1. A method of treating inflammation in patient in need thereof, comprising the step of
administering to said patient a therapeutic amount of an inhibitor of activity or formation of a PP1/GADD34 complex sufficient to reduce inflammation in said patient, wherein said inhibitor is not salubrinal and wherein said inflammation is a response in said patient selected from the group consisting of activation of dendritic cells, activation of the complement system, release of inflammatory cytokines, cytokine storm, hyperproduction of inflammatory mediators, production of chemokines, and leukocyte migration.

2. The method of claim 1, wherein said inflammation is resultant from inflammatory bowel disease.

3. The method of claim 1, wherein said inhibitor is an inhibitor of GADD34.

4. The method of claim 1, wherein said inhibitor is an inhibitor of PP1 in complex with GADD34.

5. The method of claim 1, wherein said inhibitor inhibits an interaction domain comprising amino acid residues 540 to 600 of GADD34.

6. The method of claim 1, wherein said inhibitor is selected from the group consisting of tautomycine, calyculin A, a peptide comprising a fragment of GADD34 and a peptide consisting of a fragment of GADD34.

7. The method of claim 1, wherein said inhibitor is a selective inhibitor of said PP1/GADD34 complex.

8. The method of claim 1, wherein said inflammation is not resultant from inflammatory bowel disease.

9. A method of treating inflammation in a patient in need thereof, wherein said inflammation is resultant from an inflammatory condition selected from the group consisting of allergy, asthma, myopathy, acute respiratory distress syndrome (ARDS), systemic inflammatory response syndrome (SIRS), and psoriasis, comprising the step of
administering to said patient a therapeutic amount of an inhibitor of activity or formation of a PP1/GADD34 complex sufficient to reduce inflammation in said patient, wherein said inhibitor is not salubrinal and wherein said inflammation is a response in said patient selected from the group consisting of activation of dendritic cells, activation of the complement system, release of inflammatory cytokines, cytokine storm, hyperproduction of inflammatory mediators, production of chemokines, and leukocyte migration.

10. The method of claim 9, wherein said inhibitor is an inhibitor of GADD34.

11. The method of claim 9, wherein said inhibitor is an inhibitor of PP1 in complex with GADD34.

12. The method of claim 9, wherein said inhibitor inhibits an interaction domain comprising amino acid residues 540 to 600 of GADD34.

13. The method of claim 9, wherein said inhibitor is selected from the group consisting of tautomycine, calyculin A, a peptide comprising a fragment of GADD34 and a peptide consisting of a fragment of GADD34.

14. The method of claim 9, wherein said inhibitor is a selective inhibitor of said PP1/GADD34 complex.

15. The method of claim 1, wherein said inflammatory cytokines are interferon-beta and interleukin-12.

16. The method of claim 9, wherein said inflammatory cytokines are interferon-beta and interleukin-12.

* * * * *